US010624645B2

(12) United States Patent
Matonick et al.

(10) Patent No.: US 10,624,645 B2
(45) Date of Patent: Apr. 21, 2020

(54) CIRCULAR SURGICAL STAPLERS WITH ISOLATING AND MEDICANT-RELEASING SLEEVES

(71) Applicant: Ethicon, Inc., Somerville, NJ (US)

(72) Inventors: John P. Matonick, Warren, NJ (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 439 days.

(21) Appl. No.: 15/270,468

(22) Filed: Sep. 20, 2016

(65) Prior Publication Data

US 2018/0078260 A1  Mar. 22, 2018

(51) Int. Cl.
*A61B 17/115* (2006.01)
*A61B 17/072* (2006.01)
(Continued)

(52) U.S. Cl.
CPC ........ *A61B 17/1155* (2013.01); *A61B 17/072* (2013.01); *A61B 17/1114* (2013.01);
(Continued)

(58) Field of Classification Search
CPC .............. A61B 17/1155; A61B 17/072; A61B 17/0644; A61B 17/07292;
(Continued)

(56) References Cited

U.S. PATENT DOCUMENTS 4,351,466 A * 9/1982 Noiles .................. A61B 17/115
227/8
5,250,058 A * 10/1993 Miller .................... A61B 17/11
24/615
(Continued)

FOREIGN PATENT DOCUMENTS

EP  1588667 A1  10/2005
EP  2165665 A1  3/2010
(Continued)

OTHER PUBLICATIONS

Ho, Y.-H. et al "Techniques for colorectal anastomosis", World Journal of Gastroenterology, 16(13), pp. 1610-1621 (2010).
(Continued)

*Primary Examiner* — Alex M Valvis
*Assistant Examiner* — David G Shutty
(74) *Attorney, Agent, or Firm* — David R. Crichton; Leo B. Kriksunov

(57) ABSTRACT

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, prevent tissue infection, and to prevent leakage. The present invention further relates to circular stapling instruments and elongated tubular hollow sleeves having compressible/expandable rings, deployed from such stapling instruments and estab-
(Continued)

lishing an isolated enclosure around the stapled and resected tissues at the anastomotic joint.

18 Claims, 22 Drawing Sheets

(51) Int. Cl.
  *A61B 17/11* (2006.01)
  *A61B 17/00* (2006.01)
(52) U.S. Cl.
  CPC .................. *A61B 17/07292* (2013.01); *A61B 2017/00884* (2013.01); *A61B 2017/00893* (2013.01); *A61B 2017/07257* (2013.01); *A61B 2017/07278* (2013.01); *A61B 2017/1132* (2013.01)
(58) Field of Classification Search
  CPC ........... A61B 2017/00004; A61B 2017/00336; A61B 2017/00862; A61B 2017/00884; A61B 2017/00889; A61B 2017/0725; A61B 2017/07257; A61B 2017/07278
  See application file for complete search history.

(56) References Cited

U.S. PATENT DOCUMENTS

| | | | |
|---|---|---|---|
| 5,271,544 A | 12/1993 | Fox et al. | |
| 5,839,639 A * | 11/1998 | Sauer | A61B 17/115 227/175.1 |
| 7,527,185 B2 | 5/2009 | Boaz et al. | |
| 7,776,060 B2 * | 8/2010 | Mooradian | A61B 17/115 227/180.1 |
| 7,776,081 B2 * | 8/2010 | Zuidema | A61B 46/30 623/1.23 |
| 7,886,951 B2 | 2/2011 | Hessler | |
| 8,167,895 B2 | 5/2012 | D'Agostino et al. | |
| 8,177,798 B2 * | 5/2012 | Fowler | A61B 17/11 227/179.1 |
| 8,257,391 B2 | 9/2012 | Orban, III et al. | |
| 8,286,849 B2 | 10/2012 | Bettuchi | |
| 8,372,094 B2 | 2/2013 | Bettuchi et al. | |
| 8,511,533 B2 | 8/2013 | Viola et al. | |
| 8,821,523 B2 | 9/2014 | Heinrich et al. | |
| 9,010,605 B2 | 4/2015 | Olson et al. | |
| 9,504,470 B2 * | 11/2016 | Milliman | A61B 17/07292 |
| 2010/0301098 A1 * | 12/2010 | Kostrzewski | A61B 17/07292 227/179.1 |
| 2011/0011916 A1 * | 1/2011 | Levine | A61B 17/115 227/179.1 |
| 2011/0114699 A1 * | 5/2011 | Baxter, III | A61B 46/17 227/175.1 |
| 2011/0184444 A1 * | 7/2011 | D'Agostino | A61B 17/072 606/153 |
| 2012/0241492 A1 | 9/2012 | Shelton, IV et al. | |
| 2013/0153634 A1 * | 6/2013 | Carter | A61B 17/072 227/176.1 |
| 2013/0253549 A1 * | 9/2013 | Elachchabi | A61B 17/11 606/153 |
| 2014/0252062 A1 * | 9/2014 | Mozdzierz | A61B 17/07292 227/175.1 |
| 2014/0358167 A1 * | 12/2014 | Armstrong | A61B 17/07292 606/153 |
| 2018/0078260 A1 * | 3/2018 | Matonick | A61B 17/072 |

FOREIGN PATENT DOCUMENTS

| EP | 1702570 B1 | 10/2010 |
|---|---|---|
| EP | 1929958 B1 | 9/2013 |

OTHER PUBLICATIONS

Jönsson, K. et al "Breaking strength of small intestinal anastomoses", The American Journal of Surgery, v. 145, pp. 800-803 (1983).
Morks, A.N. et al., "The C-seal: A Biofragmentable Drain Protecting the Stapled Colorectal Anastomosis from Leakage" J. Vis. Exp. (45), p. 2223 (2010).

* cited by examiner

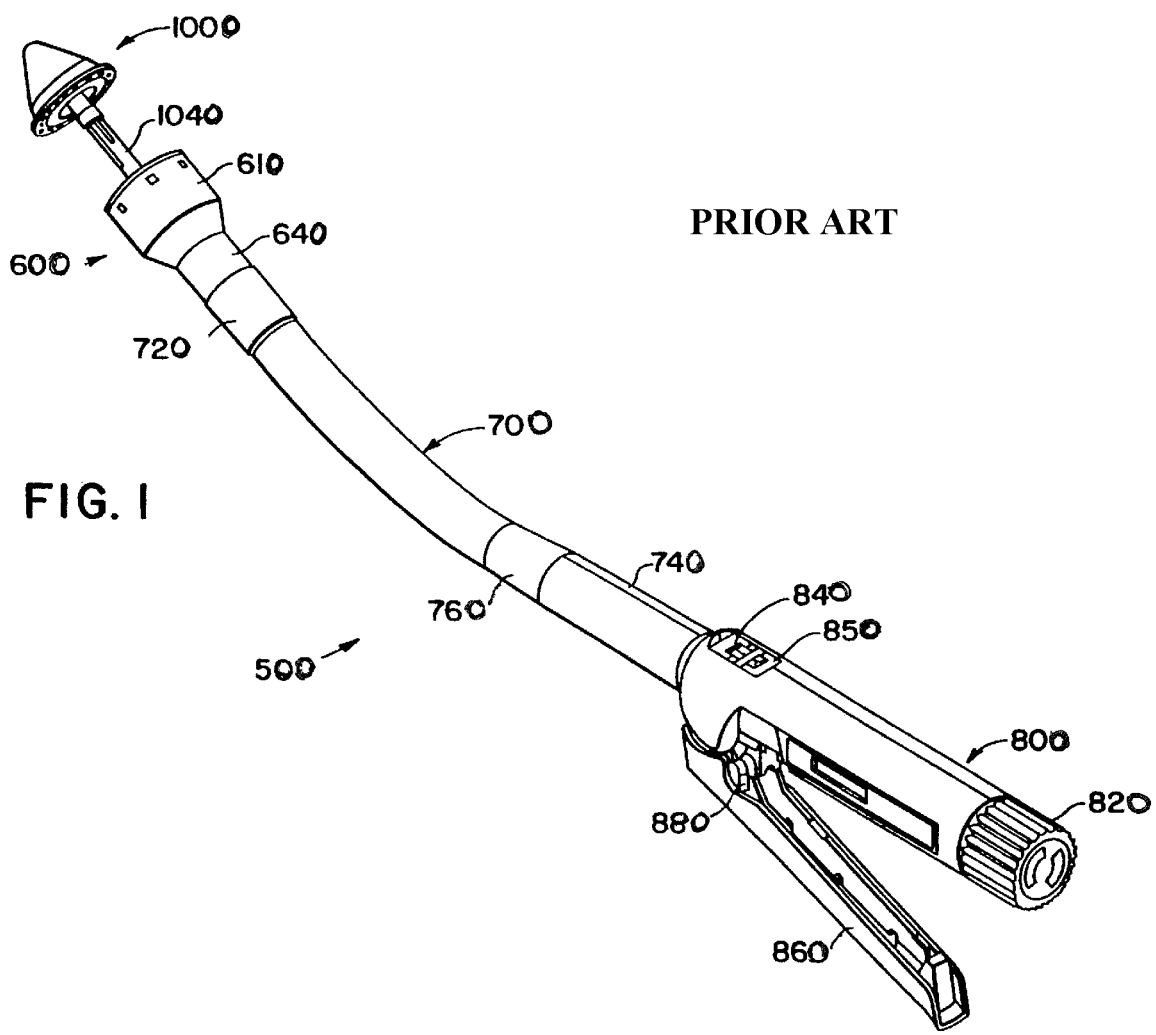

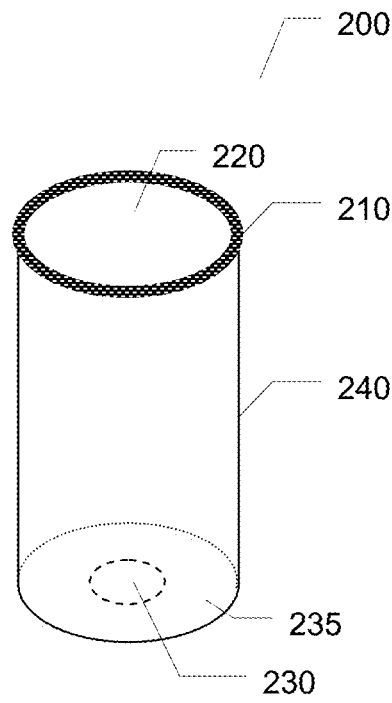
FIG. 4A
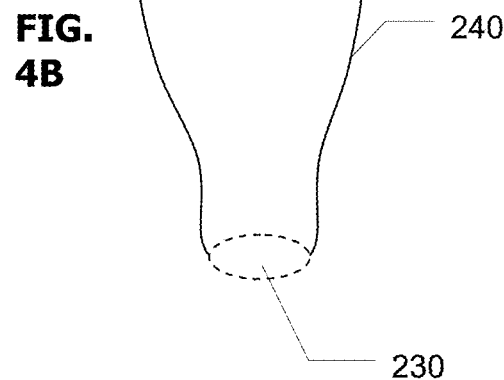
FIG. 4B
FIG. 4C
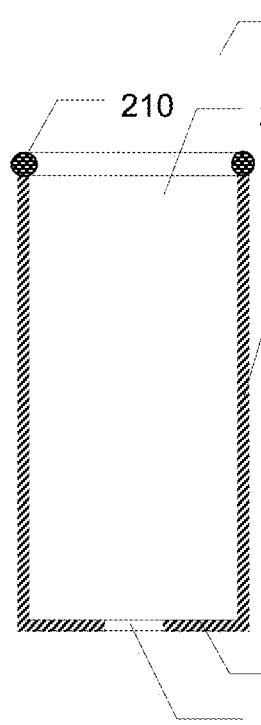
FIG. 4D
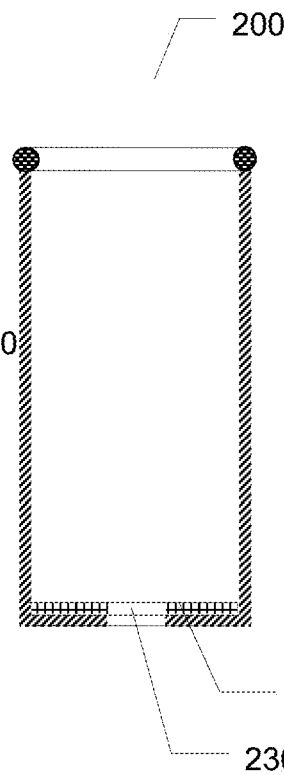
FIG. 4E
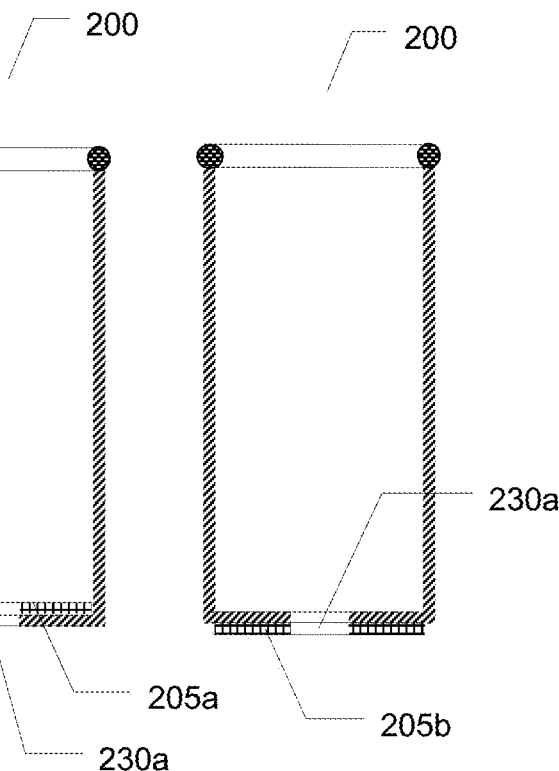

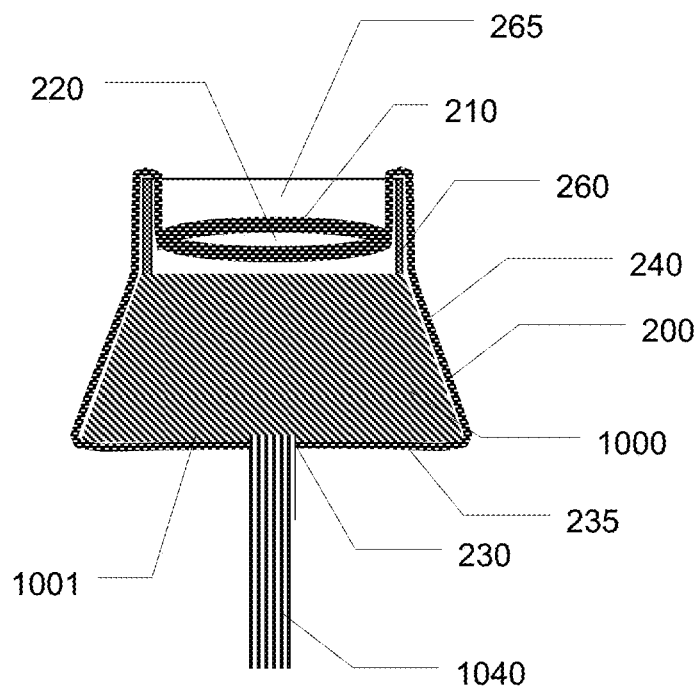
FIG. 8A
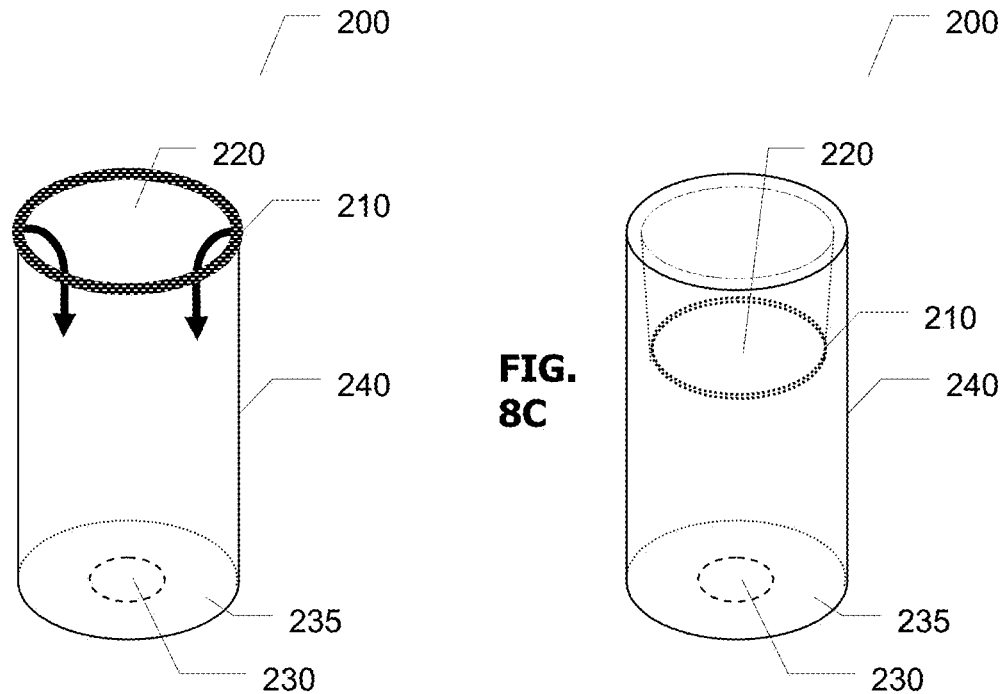
FIG. 8B
FIG. 8C

CIRCULAR SURGICAL STAPLERS WITH ISOLATING AND MEDICANT-RELEASING SLEEVES

FIELD OF THE INVENTION

The present invention relates to surgical instruments and methods for enhancing properties of tissue repaired or joined by surgical staples and, more particularly to surgical instruments and methods designed to reinforce and isolate the repaired or adjoined tissue at a target surgical site.

BACKGROUND OF THE INVENTION

Throughout the years the medical field has utilized various techniques in an effort to join or bond body tissue together. Historically, suturing was the accepted technique for rejoining severed tissues and closing wounds. Suturing is achieved with a surgical needle and a suturing thread, with the intended function of sutures to hold the edges of a wound or tissue against one another during the healing process. Staples are used to replace suturing when joining or anastomosing various body structures, such as, for example, the bowel. The surgical stapling devices employed to apply staples are generally designed to simultaneously cut and seal an extended segment of tissue in a patient.

Linear or annular/circular surgical stapling devices are employed by surgeons to sequentially or simultaneously apply one or more rows of surgical fasteners, e.g., staples, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated, firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular or circular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis in a separate step.

U.S. Pat. No. 7,776,081 entitled "Devices and methods for anastomosis" by Johan Zuidema et al. discloses a method of treating a human or animal organism comprising inserting a tube formed from a biocompatible, biodegradable polymer into a lumen at a point of a desired anastomosis, joining two ends of biological vessels together to create an anastomosis, and with one end of the tube being firmly attached to a proximal end of the anastomosis, inverting the tube by drawing the other end of the tube through the anastomosis and extending through the anastomosis such that the tube allows natural contents of the lumen to drain through and with the tube shielding the anastomosis in the organism from the natural contents of the lumen.

An article entitled "The C-seal: A Biofragmentable Drain Protecting the Stapled Colorectal Anastomosis from Leakage", by A. N. Morks et al., published in J. Vis. Exp. (45), p. 2223 (2010), discloses so called C-seal which is a biofragmentable drain, which is stapled to the anastomosis with the circular stapler.

U.S. Patent Publication 2014/0358167 "ANASTOMOTIC SLEEVE DEVICE" discloses a system for performing a medical procedure comprising: a) a stapler comprising: a detachable anvil head comprising an anvil surface and a hollow rod comprising a lumen protruding from the anvil surface, a stapler shaft comprising a stapler surface and a spike protruding from the stapler surface, and a shape cutter, wherein the anvil surface comprises a groove, wherein the stapler surface comprises a staple port and a cutter port wherein the cutter can advance through the cutter port, and wherein the spike is proportioned to fit inside the lumen of the hollow rod; and b) a support structure comprising: a first shield piece comprising a first support surface and at least one first wall comprising a first bottom edge wherein the first bottom edge is attached to the first support surface and a second shield piece comprising a second support surface, wherein the second shield piece is not attached to the first shield piece, wherein the first support surface and/or the second support surface comprises a hole, and wherein the first support surface and the second support surface align with the anvil surface and the stapler surface to provide for the delivery of a staple through the first support surface and the second support surface.

Various compression anastomotic ring systems have been pursued as a replacement to the staple-based anastomotic closure. For example, LARA™ compression anastomotic ring system developed by novoGI™ utilizes nitinol-based compression ring specifically targeting low anterior resection (LAR) procedures.

U.S. Pat. No. 7,527,185 "Compression anastomosis ring assembly and applicator for use therewith" assigned to Niti Surgical Solutions Ltd., discloses a compression anastomosis ring (CAR) assembly which comprises: a first portion which comprises: an anvil ring; and a second portion which comprises: a bottom ring positioned substantially parallel to and spaced apart from said anvil ring, said anvil ring and said bottom ring being adapted to be brought together in the presence of a closure force applied thereacross: at least one ring element, where one of said at least one ring elements is a needle ring positioned on a side of said bottom ring distal from said anvil ring, said needle ring having a plurality of needles extending generally transversely therefrom toward said first portion; and at least one spring element which provides a restorative force formed at least partially of a shape-memory alloy, said spring element positioned on one of said at least one ring elements and being in compressive force transmissive contact with said bottom ring, and wherein when said compression anastomosis ring (CAR) assembly is positioned so as to hold between said anvil ring and said bottom ring tissue portions to be compressed and joined by anastomosis, said needle ring is operative, in response to the closure force to drive said plurality of needles through the tissue portions to be compressed and to anchor said plurality of needles in said anvil ring, and wherein when said anvil ring and said bottom ring are brought together in the presence of the closure force holding the tissue portions therebetween, and when said anvil ring is anchored by said plurality of needles, the restorative force provided by said at least one spring element is operative on said bottom ring to compress said tissue portions thereby effecting anastomosis.

U.S. Pat. No. 5,250,058 "Absorbable anastomosic fastener means" assigned to ETHICON INC., discloses a mechanism which is capable of anastomosis of two lumens by an absorbable fastener. The fastener is made from two washer-like plates. One such plate has holes to receive latching prongs protruding from the other plate. Fastening is done through a single linear motion that causes the prongs to pierce the tissue, latches the prongs into a receiver and causes a knife blade to cut through excess fastener material and tissue. The ease of removal, by pulling the mechanism through the formed anastomosis, is greatly enhanced. The system can be used such that the plates can be placed in any configuration to properly anastomose tissue. The patent discloses a compression anastomosis device comprising: a piercing ring containing a plurality of piercing flanges; a receiving ring containing a plurality of receiving slots corresponding to said flanges; and spring means placed between said piercing and receiving rings to exert a spring force on one of said piercing and receiving rings.

Post-operative leakage of the stapled tissue seals, including anastomotic seals has been shown to lead to morbidity and mortality. A number of technologies are related to direct application of material to the serosal layer after stapling by either dripping or spraying. The problems associated with these techniques are that access is very difficult and visual assessment as to whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult.

U.S. Pat. No. 8,511,533 "Annular adhesive structure" discloses a surgical stapling device for joining tissue portions, comprising: a handle assembly; an anvil assembly at a distal end of the stapling device, the anvil assembly having a shaft for removably connecting the anvil assembly to the stapling device; a tubular body portion, the tubular body portion having a staple cartridge assembly containing a plurality of surgical staples in an annular array, the anvil assembly and tubular body portion being juxtaposed with respect to one another along the shaft and arranged so as to be approximated with respect to one another; and an applicator supported on the shaft of the anvil assembly, the applicator having a disc-shaped structure disposed between the anvil member and tubular body portion, the disc-shaped structure having a channel radially oriented and open at lateral sides of the disc-shaped structure, the channel being arranged for dispensing a wound treatment material.

U.S. Pat. No. 8,372,094 "Seal element for anastomosis" discloses an assembly for disposing a seal element between tissue lumens comprising: a circular surgical stapling device comprising an anvil assembly and a tubular body portion wherein the anvil assembly comprises an anvil member and a first shaft and the tubular body portion comprises a plurality of surgical staples in a circular configuration and a second shaft disposed inwardly of the surgical staples, the first shaft being attachable to the second shaft; and a seal element disposable between tissue lumens, the seal element comprising a first material and a second material wherein the first material promotes tissue ingrowth and the second material comprises a sealant.

U.S. Pat. No. 8,286,849 "Hub for positioning annular structure on a surgical device" discloses an assembly for disposing an annular structure between adjacent intestinal sections, the assembly comprising: an annular surgical stapling device having an anvil assembly and a tubular body portion, the anvil assembly having an anvil member and an anvil shaft, the tubular body portion carrying a plurality of surgical staples in an annular configuration, the tubular body portion having a connection member disposed radially inward of the surgical staples, the anvil shaft of the anvil member including a flange and being attachable to the connection member of the tubular body portion; and a hub adapted for support on the anvil shaft to engage the flange of the anvil shaft, the hub selectively receiving the anvil shaft therein, and an annular structure radially extending from the hub, the hub including a plurality of resilient fingers extending substantially in a longitudinal direction and arranged to engage the flange of the anvil shaft to position the annular structure at a location spaced a distance from a tissue contacting surface of the anvil assembly and the tubular body portion, wherein the annular structure comprises a material selected from the group consisting of: an adhesive, a sealant, a hemostat, and a medicament.

U.S. Pat. No. 8,257,391 "Annular support structures" discloses a system for joining a first body tissue and a second body tissue, the system comprising: a circular endoscopic stapling instrument having a staple cartridge assembly and an anvil assembly for approximating and joining a first body tissue to a second body tissue, and an elongated shaft extending between the staple cartridge assembly and the anvil assembly; and a reinforcing support structure supported on the shaft of the stapling instrument at a location spaced a distance from the anvil assembly and spaced a distance from the staple cartridge assembly, the reinforcing support structure having a central hub for connection to the shaft of the stapling instrument and at least one annular reinforcing ring supported on the central hub so that the at least one annular reinforcing ring is supported on the shaft at a location between the first body tissue and the second body tissue, wherein the at least one annular reinforcing ring includes a radial outer ring and a radial inner ring, the reinforcing support structure including at least one support spoke integrally extending between the radial inner ring and the central hub, and wherein, after firing of the stapling instrument, the at least one annular reinforcing ring is interposed between and reinforces the joined first body tissue and the second body tissue.

U.S. Pat. No. 8,167,895 "Anastomosis composite gasket" discloses a method of forming an anastomosis between intestinal tissue sections, comprising the steps of: providing a circular surgical anastomosis device, the circular surgical anastomosis device including: an anvil assembly having an anvil member; and a tubular body portion having an annular knife operatively disposed therein and a shaft disposed radially inward of the annular knife, the anvil assembly being attached to the shaft of the tubular body; inserting the anvil assembly into a first intestinal section; inserting the tubular body portion into a second intestinal section; disposing a structure, including at least a first ring of a first material, a second ring of a second material, and a third ring between the first intestinal section and the second intestinal section, the first ring comprising a disk having an aperture and the second ring comprising a disk having an aperture, the second ring having an outer perimeter, wherein the outer perimeter of the second ring is directly attached to the first ring and disposed within the aperture of the first ring, and the third ring radially extending outward from the first ring and beyond staple retaining slots of the tubular body portion, the structure possessing a wound treatment material consisting of at least one of an adhesive and a sealant; and firing staples through the intestinal tissue sections and through the structure.

U.S. Pat. No. 7,886,951 "Pouch used to deliver medication when ruptured" discloses an anvil assembly for a circular stapling device, the anvil assembly comprising: an anvil head configured to support an anvil plate thereon; a shaft extending from the anvil head and configured to selectively engage a rod member of the circular stapling device; an anvil plate operatively connected to the anvil head, wherein the anvil plate includes an inner diametral edge, and wherein the anvil plate defines a plurality of staple forming pockets therein at a location radially outward of the inner diametral edge; a recess formed in the anvil head, wherein the recess is defined by the inner diametral edge of the anvil plate and a rear surface of the anvil head; and a wound treatment material disposed substantially within the recess.

U.S. Patent Publication No. 2012/0241492 "TISSUE THICKNESS COMPENSATOR COMPRISING AT LEAST ONE MEDICAMENT" discloses a stapling assembly for use with a stapler, said stapling assembly comprising: an anvil comprising a plurality of forming surfaces; a compensator attached to said anvil, wherein said compensator comprises a plurality of cavities aligned with said forming surfaces; and at least one medicament positioned within each said cavity.

U.S. Pat. No. 8,821,523 "Structure for applying sprayable wound treatment material" discloses a guard for use in combination with an anastomotic surgical stapling apparatus, wherein the surgical stapling apparatus is configured and adapted to dispense staples from a staple pusher member of a body portion of the surgical stapling apparatus and to deliver wound treatment material from a stem of an anvil assembly of the surgical stapling apparatus to a target surgical site, wherein the guard comprises: a central hub defining a lumen therethrough for receiving the stem of the anvil assembly of the surgical stapling apparatus; an annular cuff supported by the central hub and extending at least substantially therearound, wherein the annular cuff is configured to be disposed radially outward of a staple line of the surgical stapling apparatus, and wherein the annular cuff defines an arcuate upper lip connected to an arcuate lower lip; and an annular flange extending radially inwardly from a radially-outermost portion of the annular cuff, the annular flange being positioned for staples to be fired therethrough.

U.S. Pat. No. 9,010,605 "Sliding sleeve for circular stapling instrument reloads" discloses a surgical stapling device for joining tissue portions, comprising: a handle assembly; an elongate body extending from the handle assembly; a cartridge assembly supported on a distal end of the elongate body, the cartridge assembly including a staple cartridge containing a plurality of surgical staples in an annular array; an anvil assembly at a distal end of the surgical stapling device, the anvil assembly having a shaft for removably coupling the anvil assembly to the cartridge assembly and a head pivotally mounted to a distal end of the shaft, the anvil assembly translatable relative to the cartridge assembly between a first position, where the anvil assembly is spaced from the cartridge assembly, and a second position, where the anvil assembly is approximated relative to the cartridge assembly for clamping tissue therebetween, the head of the anvil assembly transitionable between a first condition, where a tissue contacting surface of the head is substantially perpendicular to the shaft, and a second condition, where the tissue contacting surface of the head is tilted relative to the shaft; and a sleeve member slidably disposed about the shaft of the anvil assembly, the sleeve member transitionable between a first position, where the sleeve member engages the head of the anvil assembly to secure the head in the first condition, and a second position, where the sleeve member is disengaged from the head of the anvil assembly to allow the head to transition to the second condition.

There is a need to deliver medicants in the area of the anastomotic joint for localized release to prevent ulceration and leaks, however it is difficult to create the necessary concentrations of medicants in an open area. Further, there is a need to temporary isolate anastomotic joint form the environment of the GI tract.

The known systems of isolating anastomotic joints can be complex and unable to fully isolate areas of resected and stapled tissue. The staple based anastomotic joining is a widely accepted practice but there is a need in improving the technology to prevent post-operative leakage of the stapled tissue seals to improve the viability of the tissue joined by staples.

SUMMARY OF THE INVENTION

The present invention relates to surgical instruments and methods for enhancing properties of tissue repaired or joined by surgical staples and, more particularly to surgical instruments and methods designed to enhance the properties of repaired or adjoined tissue at a target surgical site, especially when sealing an anastomosis between adjacent intestinal sections so as to improve tissue viability, and reduce the occurrence of tissue infection and leakage.

Tubular polymeric sleeves, optionally impregnated with a medically useful agent, are carried on the anvil and/or on the stapling head and are stapled to the anastomotic joint as the anastomosis is performed. The sleeves are then left in the lumen after the stapling and removal of the circular stapler, creating an isolating enclosure around the anastomotic joint. The sleeves are optionally releasing medicants such as antibiotic agents and/or microflora into the isolating enclosure thus treating the tissue in the areas proximal to the anastomotic joint, including stapled tissue, resected tissue, and surrounding tissue.

The present invention, in one aspect, relates to a circular surgical stapler for anastomotic joining of tissue having a stapling head connected to an opposing anvil, with stapling head containing a plurality of deployable staples in concentric arrays, and to an isolating sleeve deployable from the stapler onto the stapled anastomotic joint. In one embodiment, a circular stapling instrument comprises an anvil having a tissue facing end and an opposite distal end, with an anvil sleeve retainer positioned on the distal end thereof; a cylindrical stapling head mounted on a support shaft, said stapling head containing a plurality of deployable staples in concentric arrays on a tissue facing side and a concentric knife; a moveable shaft connecting the anvil and stapling head; and an elongated tubular hollow anvil sleeve, wherein said anvil sleeve has a compressible/expandable anvil ring at a distal end thereof, said anvil sleeve is releasably mounted on said anvil and at least partially enveloping said anvil, said anvil ring is compressed and releasably engaged by the anvil sleeve retainer and a portion of said anvil sleeve is disposed on the tissue facing end of said anvil. The anvil sleeve retainer can be a hollow cup having diameter smaller than diameter of said cylindrical stapling head or a ring-shaped cavity having diameter smaller than diameter of said cylindrical stapling head. The anvil sleeve at the distal end thereof can be inverted or turned outside-in and releasably packed into said anvil sleeve retainer.

The anvil sleeve can have an opening at a proximal end thereof that is configured to allow feeding through said opening said moveable shaft. The anvil sleeve can further comprise a buttress disposed at the tissue facing end of said anvil. Preferably, at least a portion of said anvil sleeve is erodible, dissolvable, or resorbable in a mammalian gastrointestinal tract over a period ranging from 1 to 8 weeks. Preferably, the anvil ring is erodible, dissolvable, or resorbable in a mammalian gastrointestinal tract over a period ranging from 1 to 8 weeks. The anvil sleeve can be at least partially coated or impregnated with a releasable anti-bacterial, anti-microbial, anti-infective agent, bacterial culture, or combinations thereof.

The circular stapling instrument can further comprise an elongated tubular hollow stapling head sleeve that is releasably mounted on said stapling head and at least partially envelopes said stapling head and a portion of said stapling head sleeve is disposed on the a tissue facing side of said stapling head. The stapling head sleeve can further comprise a compressible/expandable stapling head sleeve ring at a proximal end thereof. The circular stapling instrument can further comprise a stapling head sleeve retainer that is positioned on the support shaft and configured to releasably engage said stapling head sleeve. The stapling head sleeve retainer can have a hollow frustoconical or a hollow cylindrical form and form a ring-shaped cavity around said support shaft, wherein the diameter of said ring-shaped cavity is smaller than diameter of said cylindrical stapling head. The compressible/expandable stapling head sleeve ring can be radially compressed to a diameter smaller than diameter of said cylindrical stapling head. The stapling head sleeve can have an opening at a distal end thereof that is configured to allow feeding through said opening said moveable shaft. The stapling head sleeve can further comprise a buttress disposed at the tissue facing side of said stapling head. Preferably, at least a portion of the stapling head sleeve is erodible, dissolvable, or resorbable in a mammalian gastrointestinal tract over a period ranging from 1 to 8 weeks.

The present invention is also directed to methods of establishing an anastomotic joint between tubular tissue lumens with an anastomotic stapler, the stapler having a stapling head containing a plurality of deployable staples by axially positioning a hollow tubular anvil sleeve having a compressible/expandable anvil ring on one end thereof on the anvil and releasably engaging said compressible/expandable anvil ring in an anvil sleeve retainer mounted on said anvil; axially inserting said anvil into a first tubular tissue and closing said first tubular tissue around said anvil; axially inserting said stapling head into a second tubular tissue; connecting said anvil to said stapling head via an anvil shaft; approximating said anvil and said stapling head to compress said first and second tubular tissues between said stapling head and said anvil; firing said anastomotic stapler to form a stapled anastomotic joint between said first and second tubular tissues and simultaneously stapling said anvil sleeve to said first and second tubular tissues; withdrawing said anastomotic stapler from said first and second tubular tissues to release said compressible/expandable anvil ring form said anvil sleeve retainer and leave said anvil sleeve inside said first and second tubular tissues; turning and inverting said anvil sleeve outside-in; extending said anvil sleeve from said first tubular tissue into said second tubular tissue; expanding said compressible/expandable anvil ring to push against said second tissue lumen inside surface; and leaving said anvil sleeve inside said first and second tubular tissues for sufficient time for at least partial healing of said tissues at the anastomotic joint.

BRIEF DESCRIPTION OF THE FIGURES

FIG. 1 shows a perspective view of a typical circular surgical stapling instrument.

FIGS. 4A-E show schematic perspective and cross-sectional views of anvil sleeve of the present invention.

FIGS. 8A-C show schematic perspective and cross-sectional views of anvil sleeve and anvil of the present invention.

DETAILED DESCRIPTION OF THE INVENTION

Figure 2A:
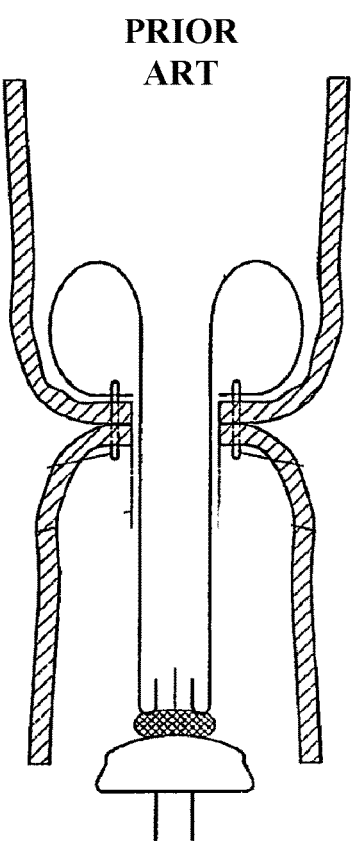
FIGS. 2A-C show cross-sectional views taken from FIGS. 4, 5, 6 of U.S. Pat. No. 7,776,081 entitled "Devices and methods for anastomosis".

Surgery often involves joining of two or more layers of tissue together with optional simultaneous sectioning of a portion of the tissue along the staple line. For example, colorectal surgery in many cases involves the resection of a segment of the colon and rectum. Following a colorectal resection, the colon and rectum are drawn together with a circular stapler and an end-to-end anastomosis is performed. Post-operative leakage of the anastomosis has been shown to lead to morbidity and mortality.

Typical surgical stapling instruments have a staple-containing component and an opposing anvil component, between which at least two tissue layers to be joined are compressed prior to delivery of staples from the staple-containing component, whereby staples are piercing both tissue layers and are bent, deformed, or closed against the opposing anvil component.

Referring now to FIG. 1, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 500 includes a distal stapling head assembly 600 connected by a longitudinally curved support shaft assembly 700 to a proximal actuator handle assembly 800. The stapling instrument includes an anvil assembly or anvil 1000 which is slidable longitudinally relative to the stapling head assembly 600 and mounted on an axially extending moveable shaft 1040. An optional rotatable adjusting knob 820 is provided at the proximal end of the actuator handle assembly 800 for adjusting the spacing between the stapling head assembly 600 and the anvil assembly 1000. Other approximating means to compress adjacent sections of tissue are known to skilled artisans and can be used. An optional movable indicator 840 is visible through an optional window 850 on top of the handle assembly 800 to indicate the staple height and/or gap between the stapling head assembly 600 and anvil 1000 selected by rotation of the adjusting knob 820. The indicator 840 is movable indicating that the anvil gap is within a desired operating range of the stapling instrument 500. The position of the indicator 840 also indicates whether the selected staple height is large or small.

A staple actuating lever 860 is pivotally mounted on the actuator handle assembly 800 for driving the surgical staples from the stapling head assembly 600 when the anvil assembly 1000 is closed to provide the desired staple height. A pivotal latching member 880 is mounted on the handle assembly 800 for locking the staple actuating lever 860 against movement to preclude actuation of the stapling head assembly 600 when the anvil gap is outside of a predetermined range. The stapling head assembly 600 includes a tubular casing 610 as well as a hollow tubular connector 640 at the proximal end of the casing 610 which receives the distal end of the support shaft 700. A ferrule or sleeve 720 overlaps the joint between the tubular connector 640 and the distal end of the support shaft 700. The proximal end of the support shaft 700 is received by a tubular extension 740 at the distal end of the actuator handle assembly 800. A ferrule or sleeve 760 overlaps the joint between the proximal end of the support shaft 700 and the distal end of the tubular extension 740. The movable indicator 840 is visible through a window 850 on top of the handle assembly 800 to indicate the staple height selected by rotation of the adjusting knob 820.

Other versions and modifications of the circular surgical stapler are known to a skilled artisan. There are typically at least two and frequently more concentric stapling lines or concentric circular rows of staples-containing slots surrounding shaft 1040, with staples in each row typically staggered or offset relative to the staples in the adjacent row, to improve the sealing and prevent leakage along the stapling line.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jönsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

Figure 2B:
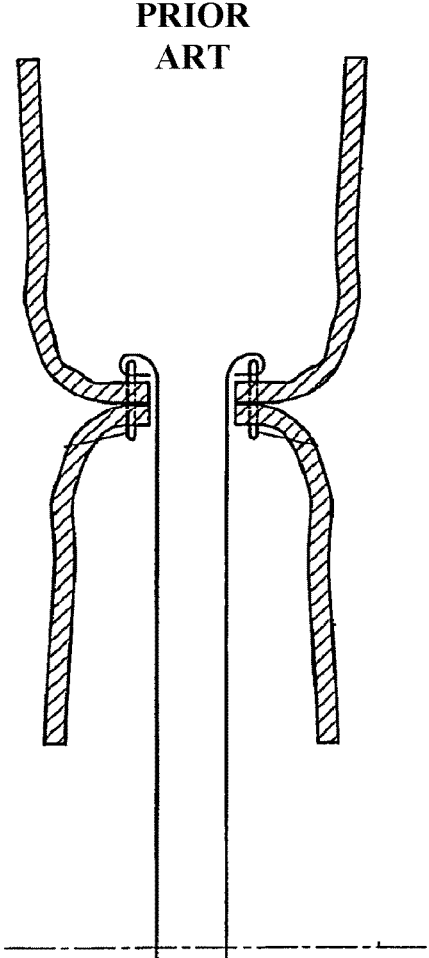
Figure 2C:
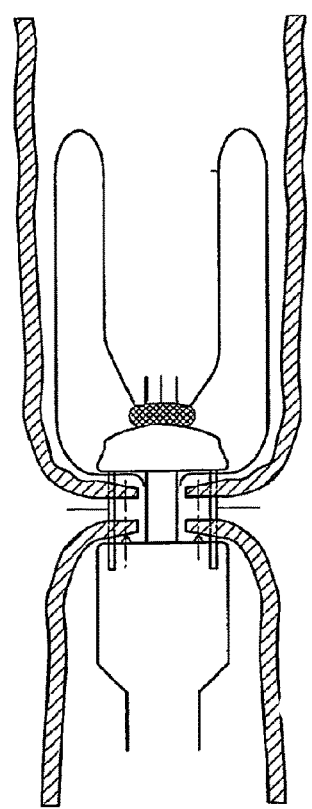
Figure 3:
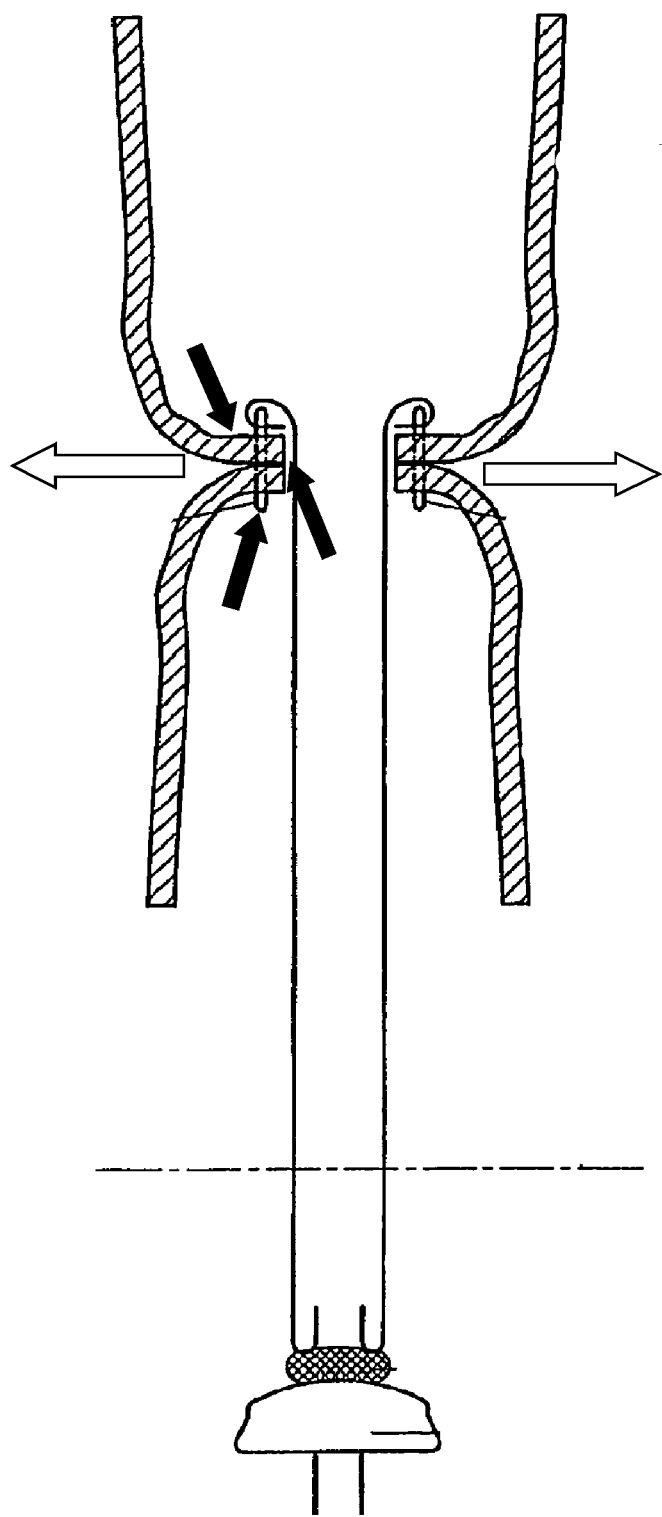
FIG. 3 shows cross-sectional view taken from FIG. 6 of U.S. Pat. No. 7,776,081 entitled "Devices and methods for anastomosis" with additional arrow indicators.

Referring now to FIG. 2, tubular shaped colorectal drain of U.S. Pat. No. 7,776,081 is shown, whereby FIGS. 4, 5 and 6 of said patent are reproduced, showing the device stapled to the anastomotic joint. Referring now to FIG. 3, whereby FIG. 6 of said patent is again reproduced with added arrows indicating deficiencies of the device. Specifically, small dark arrows show areas that the device fails to isolate (specifically the stapled areas of tissue and cut areas of tissue) from the exposure to intestinal environment and/or microflora. Large white arrows schematically indicate that the device fails to prevent leakage if the anastomotic joint is transiently leaking.

Briefly, according to the present invention, an isolating sleeve or sleeves is/are positioned on the circular anastomotic stapler and deployed with one end of the sleeve stapled to the anastomotic joint as the staples from a circular anastomotic stapler are deployed and an anastomotic joint is established connecting two parts of a tissue lumen. As the circular anastomotic stapler is withdrawn, the sleeve or sleeves is/are released from the stapler and cover and isolate the areas of tubular tissue that were stapled together, providing additional reinforcement and particularly isolating the just stapled and just resected areas from contaminations and potential infection. Optionally, a medicant is released from the sleeve into the pocket areas formed between the sleeve and the tissue, such medicant being for instance an anti-bacterial or anti-infective agent.

Referring now to FIG. 4A, showing embodiments of the present invention, a schematic perspective view of generally hollow, cylindrical shaped, flexible, and tubular anvil sleeve 200 of the present invention is shown, with anvil sleeve 200 formed by wall 240 connecting distal compressible/expandable ring 210 having distal sleeve opening 220 to optional proximal flange 235 having proximal opening 230 formed in proximal flange 235. FIG. 4B shows a schematic perspective view of the same anvil sleeve 200 having frustoconical shape with wider portion at distal compressible/expandable ring 210, with anvil sleeve 200 having no optional proximal flange 235 with tubular sleeve wall 240 terminating distally with distal sleeve opening 220 formed by compressible/expandable ring 210, and terminating proximally with proximal opening 230.

Referring to FIG. 4C, a schematic cross-sectional view of anvil sleeve 200 of FIG. 4A is shown. FIG. 4D shows another embodiment of anvil sleeve 200 having a reinforcing buttress 205*a* installed inside anvil sleeve 200 onto flange 235, with buttress having an opening 230*a* registered with proximal opening 230. FIG. 4E shows another embodiment of anvil sleeve 200 having a similar reinforcing buttress 205b which is installed outside anvil sleeve 200 onto flange 235. Buttress can also prevent radial distention which can cause high tension of the tissue at the joint. Buttress can also help to spread coverage by anvil sleeve 200.

Figure 5A:
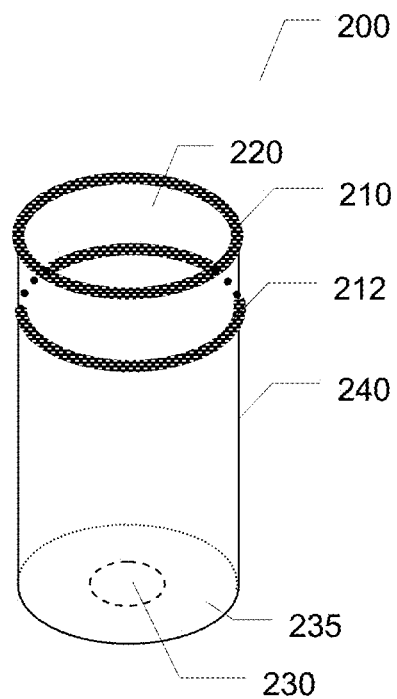
FIGS. 5A-D show schematic perspective and cross-sectional views of anvil sleeve of the present invention.

Turning now to FIG. 5A, a schematic perspective view of an embodiment of anvil sleeve 200 of the present invention is shown, with anvil sleeve 200 having additional compressible/expandable ring 212 positioned between distal compressible/expandable ring 210 and proximal opening 230. Additional compressible/expandable ring 212 is positioned proximal to compressible/expandable ring 210 and provides reinforcing for sealing afforded by compressible/expandable ring 210. FIG. 5C shows the embodiment of FIG. 5A in a schematic cross-sectional view.

Figure 5B:
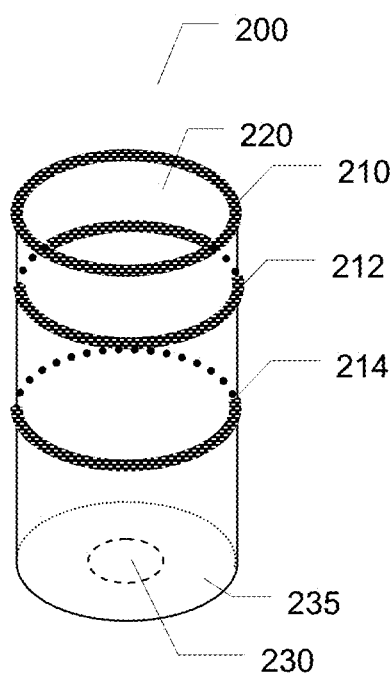
Figure 5C:
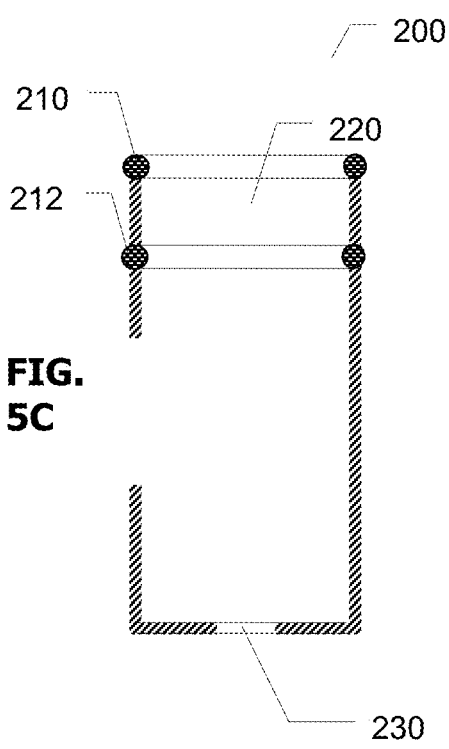
Figure 5D:
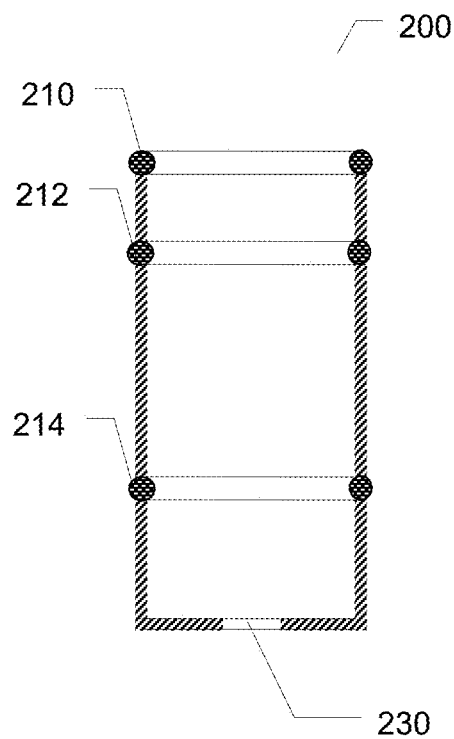

Turning now to FIG. 5B, a schematic perspective view of an embodiment of anvil sleeve 200 of the present invention is shown, with anvil sleeve 200 having compressible/expandable rings 210, 212 as in the embodiment of FIGS. 5A and 5C, and having another compressible/expandable ring 214 positioned between compressible/expandable ring 212 and proximal opening 230. Compressible/expandable ring 214 is positioned proximal to proximal opening 230. FIG. 5D shows the embodiment of FIG. 5B in a schematic cross-sectional view.

Figure 6A:
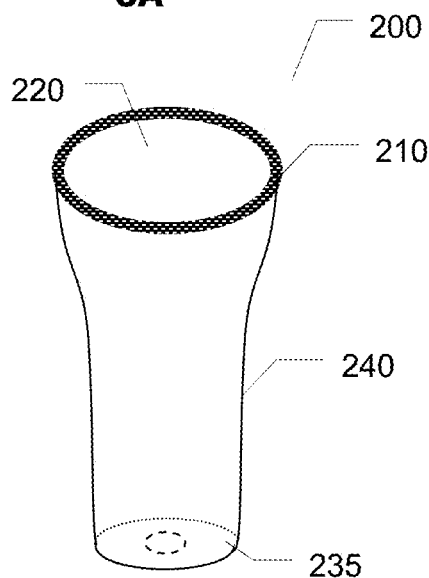
FIGS. 6A-C show schematic perspective views of anvil sleeve of the present invention.
Figure 6B:
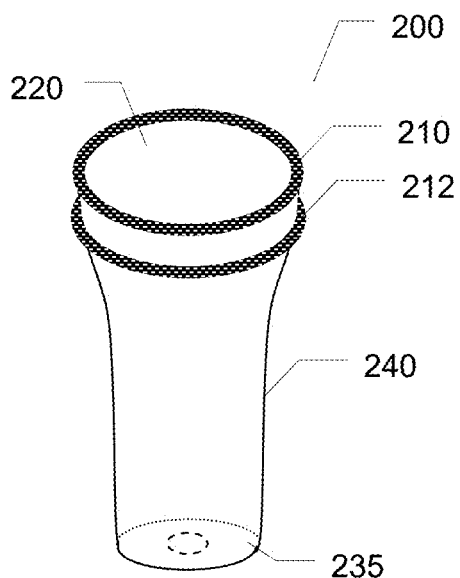

Turning now to FIG. 6A, another embodiment of anvil sleeve 200 of the present invention is shown in a schematic perspective view, with hollow, flexible, and tubular anvil sleeve 200 of the present invention having wider distal portion near distal compressible/expandable ring 210 in its expanded form, and having narrower proximal portion near optional proximal flange 235 and near proximal opening 230. FIG. 6B shows another embodiment of anvil sleeve 200 of the present invention, having additional compressible/expandable ring 212 positioned between distal compressible/expandable ring 210 and proximal opening 230, with compressible/expandable ring 212 positioned near distal compressible/expandable ring 210.

Figure 6C:
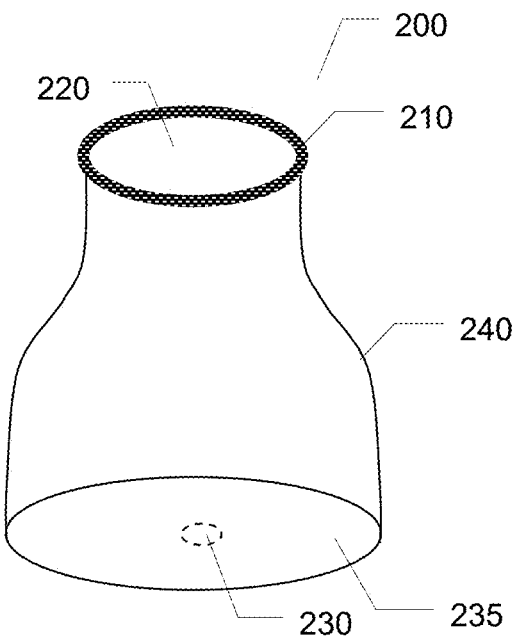

FIG. 6C shows another embodiment of anvil sleeve 200 of the present invention in a schematic perspective view, with hollow, flexible, and frustoconical anvil sleeve 200 having wider portion at proximal flange 235 and having narrower portion at distal compressible/expandable ring 210 when distal compressible/expandable ring 210 is compressed radially, with overall shape configured to fit over anvil 1000.

Figure 7A:
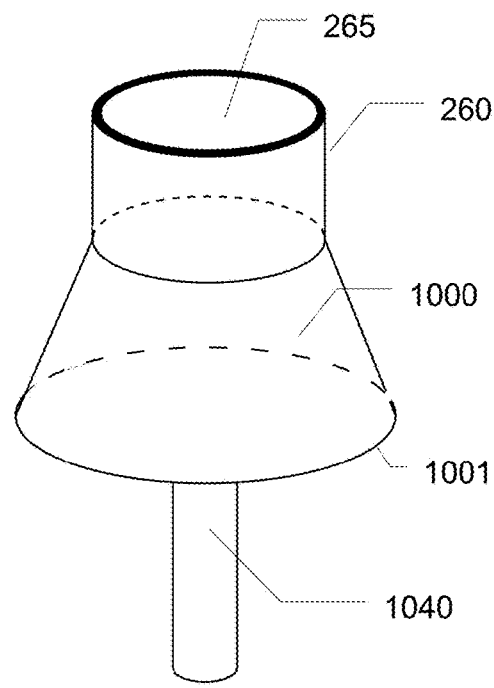
FIGS. 7A-D show schematic perspective and cross-sectional views of anvil of the present invention.
Figure 7B:
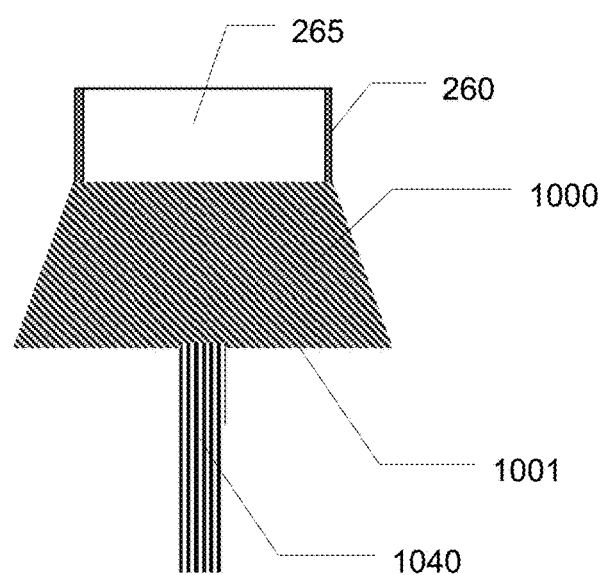

Referring now to FIG. 7A, a schematic perspective view of stapler anvil 1000 of present invention is shown, with moveable shaft 1040. Anvil 1000 has on its distal portion mounted an anvil sleeve retainer 260, having generally cylindrical cup-shaped form. Anvil sleeve retainer 260 was not shown in FIG. 1 where a generic surgical anastomosis stapling instrument was presented. Sleeve retainer 260 has a cavity 265 configured to be able to engage and hold a portion of anvil sleeve 200 with one or more compressible/expandable rings, such as distal compressible/expandable ring 210, with compressible/expandable ring fitting into cavity 265 in a radially compressed configuration. The inner diameter of cavity 265 is smaller than the outside diameter of compressible/expandable ring 210 when compressible/expandable ring 210 is fully expanded. FIG. 7B shows the embodiment of FIG. 7A in a schematic cross-sectional view.

Figure 7C:
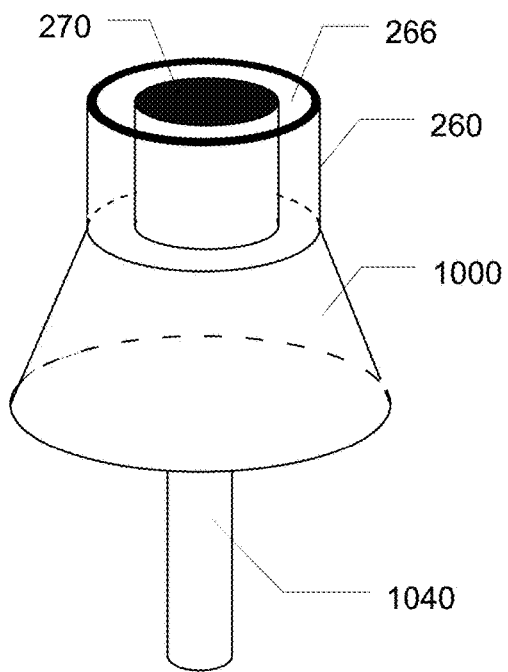
Figure 7D:
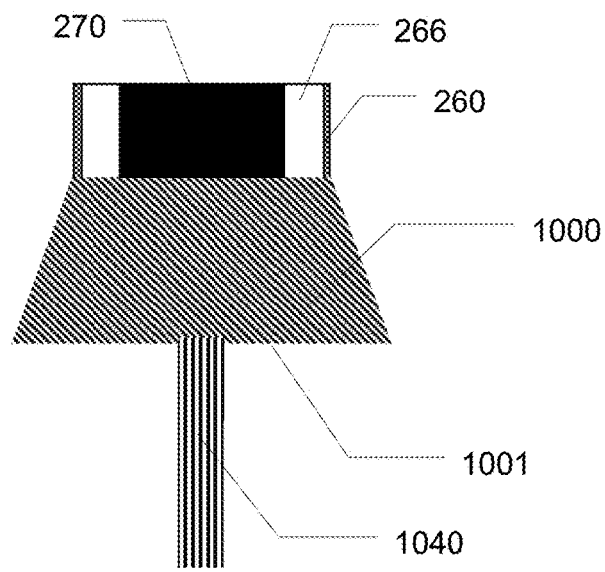

Referring now to FIGS. 7C-7D, an alternative embodiment of stapler anvil 1000 of present invention is shown in a schematic perspective view and a schematic cross-sectional view respectfully. Anvil 1000 has on its distal portion mounted a sleeve retainer 260, with a post 270 coaxially mounted inside sleeve retainer 260 thus forming a ring-shaped cavity 266 configured to be able to engage and hold a portion of anvil sleeve 200 with one or more compressible/expandable rings, such as distal compressible/expandable ring 210, with compressible/expandable ring fitting into cavity 266 in a radially compressed configuration. The inner diameter of sleeve retainer 260 is smaller than the outside diameter of compressible/expandable ring 210 when compressible/expandable ring 210 is fully expanded. FIG. 7B shows the embodiment of FIG. 7A in a schematic cross-sectional view.

Referring now to FIG. 8, mounting of anvil sleeve 200 onto anvil 1000 is shown. FIG. 8A shows a schematic cross-sectional view of anvil 1000 with anvil sleeve 200 mounted. Moveable shaft 1040 passes through proximal opening 230 with proximal flange 235 positioned against staples facing surface 1001 of anvil 1000. Sleeve wall 240 wraps around anvil 1000 and sleeve distal portion is then inverted and folded inward with compressible/expandable ring 210 radially compressed to fit into cavity 265 of sleeve retainer 260.

FIG. 8B shows a schematic perspective view of anvil sleeve 200 with arrows indicating how anvil sleeve 200 distal portion with distal compressible/expandable ring 210 is folded inward and compressed. FIG. 8C shows a schematic perspective view of the resulting configuration of anvil sleeve 200 without showing anvil 1000, with anvil sleeve 200 distal portion with distal compressible/expandable ring 210 folded inward and radially compressed. Thus when mounted on anvil 1000, anvil sleeve 200 is releasably engaged inside cavity 265 of sleeve retainer 260 via anvil sleeve 200 distal portion with distal compressible/expandable ring 210.

Figure 9:
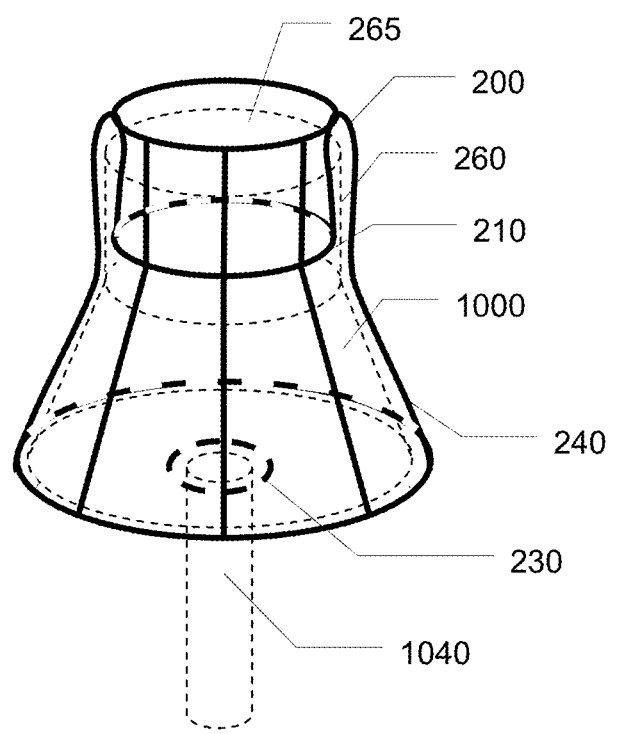
FIG. 9 shows schematic perspective views of anvil sleeve and anvil of the present invention.

FIG. 9 shows the embodiments of FIG. 8A-C in a schematic perspective view with anvil sleeve 200 (shown in bold lines) mounted on anvil 1000 (is shown in fine dashed lines), showing how anvil sleeve 200 distal portion with distal compressible/expandable ring 210 is folded inward and radially compressed and releasably engaged inside cavity 265 of sleeve retainer 260.

As shown above, anvil sleeve 200 which is made of polymeric, flexible, and at least partially elastic materials, is configured to releasably fit onto and around anvil 1000 with anvil 1000 substantially enveloped by anvil sleeve 200 and positioned substantially inside hollow tubular anvil sleeve 200.

Figure 10A:
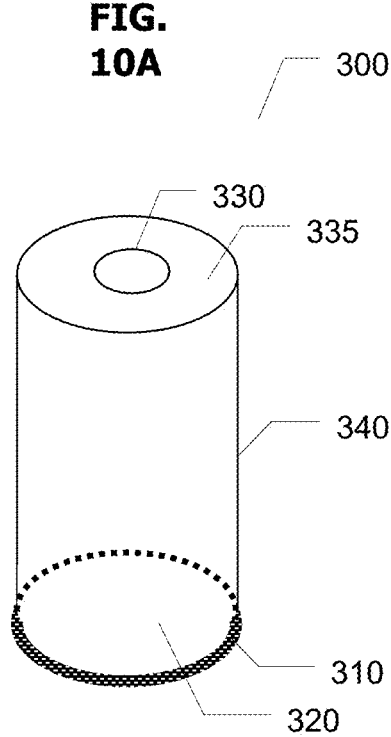
FIGS. 10A-C show schematic perspective and cross-sectional views of stapling head sleeve of the present invention.
Figure 10B:
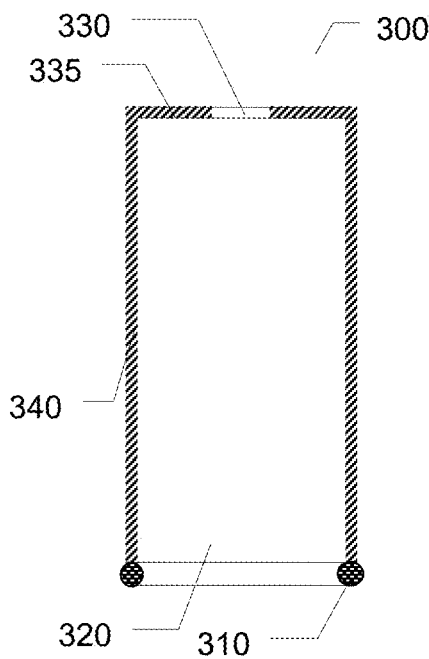
Figure 10C:
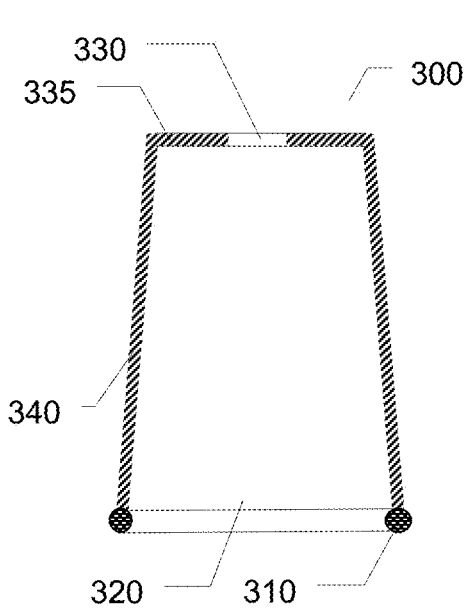

Referring now to FIG. 10A, showing embodiments of the present invention, a schematic perspective view of generally hollow, cylindrical shaped, flexible, and tubular stapling head sleeve 300 of the present invention is shown, with stapling head sleeve 300 formed by wall 340 connecting optional proximal compressible/expandable ring 310 having proximal sleeve opening 320 to distal flange 335 having distal opening 330 formed in distal flange 335. Referring to FIG. 10B, a schematic cross-sectional view of stapling head sleeve 300 of FIG. 9A is shown. Referring to FIG. 10C, a schematic cross-sectional view of stapling head sleeve 300 having a frustoconical shape with wider portion at optional proximal compressible/expandable ring 310 and narrower portion at distal flange 335.

Optionally, a reinforcing buttress (not shown) can be installed inside or outside stapling head sleeve 300 onto flange 335, with buttress having an opening registered with distal opening 330, resulting in similar structures to ones shown in FIGS. 4D and 4E for anvil sleeve 200.

Figure 11A:
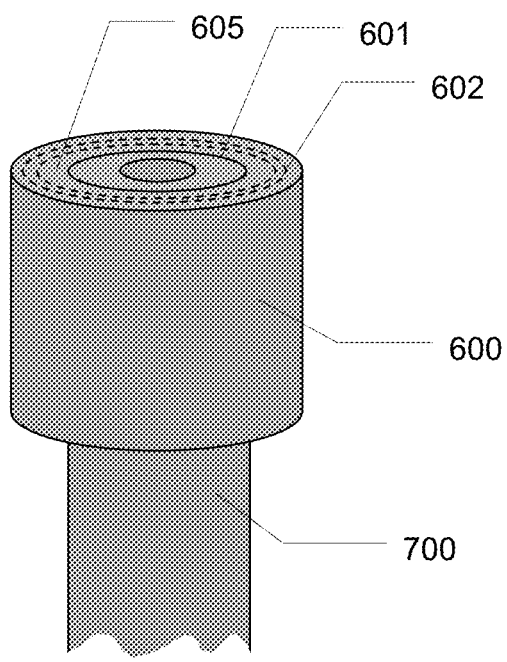
FIGS. 11A-B show schematic perspective and cross-sectional views of stapling head and stapling head sleeve of the present invention.

Referring now to FIG. 11A, a schematic perspective view of stapling head 600 is shown, with staple pockets 602 arranged in concentric arrays around tissue cutting concentric knife 601 on tissue facing surface 605.

Figure 11B:
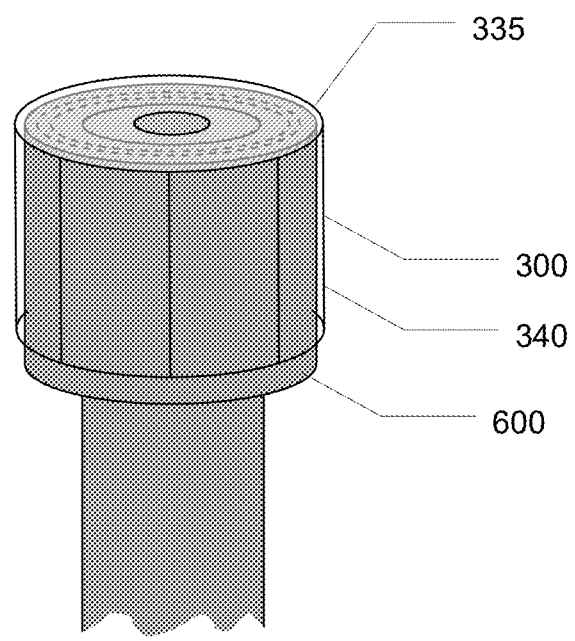

FIG. 11B shows mounting of stapling head sleeve 300 on stapling head 600 with flange 335 positioned against tissue facing surface 605 and sleeve wall 340 is wrapped around stapling head 600. In this embodiment, stapling head sleeve 300 has no optional proximal compressible/expandable ring 310.

Figure 12:
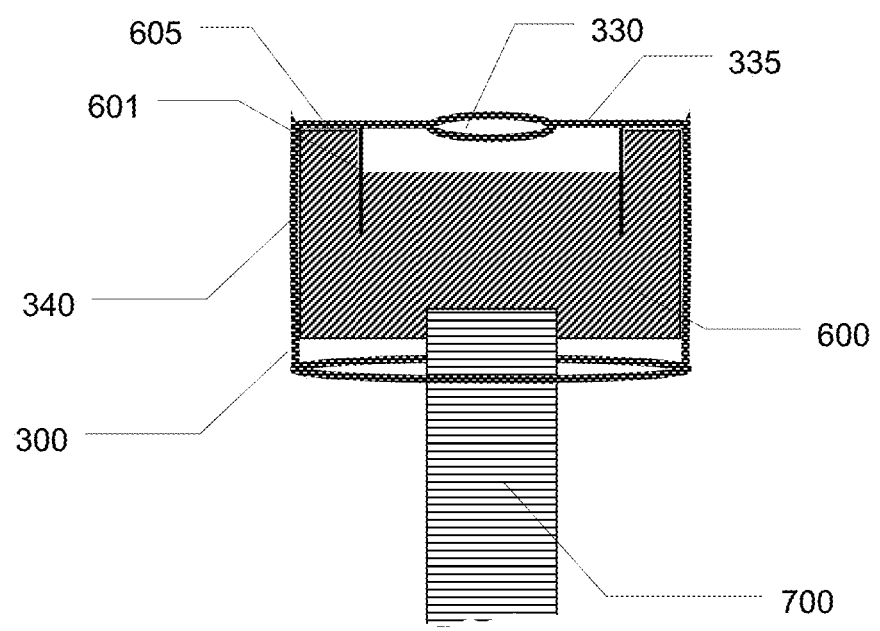
FIG. 12 shows schematic cross-sectional view of stapling head and stapling head sleeve of the present invention.

FIG. 12 shows a schematic cross-sectional view of the embodiment of FIG. 11B, with stapling head sleeve 300 mounted onto stapling head 600. In this embodiment, stapling head sleeve 300 has no optional proximal compressible/expandable ring 310. Staples, staple pockets, and mechanism of staples deployments are not shown for simplification.

Figure 13A:
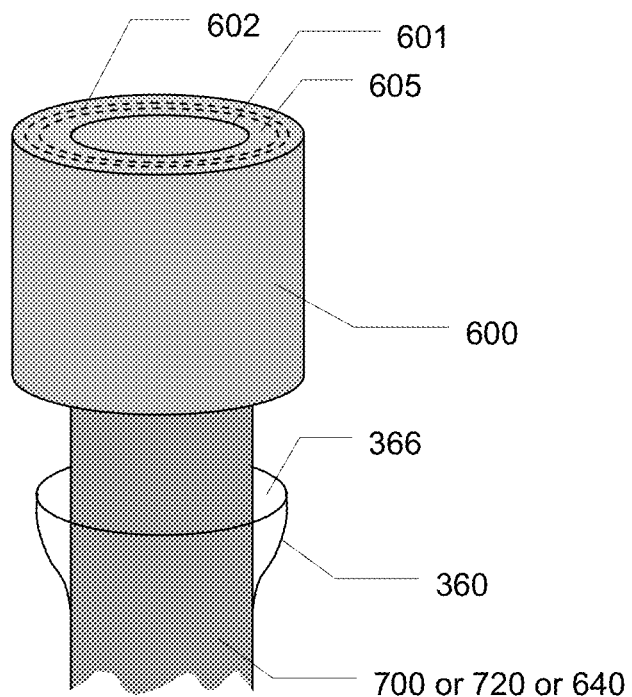
FIGS. 13A-B show schematic perspective views of stapling head of the present invention.
Figure 13B:
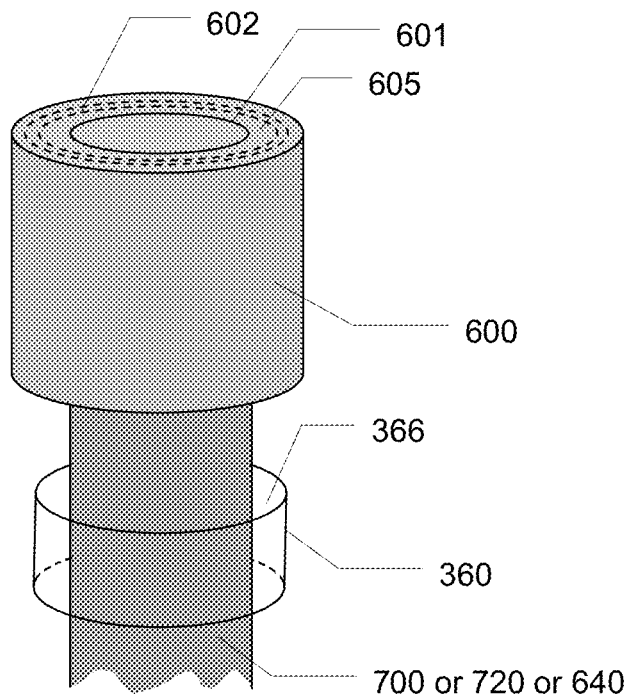

Referring now to FIGS. 13A, 13B alternative embodiments of stapling head 600 of present invention are shown in a schematic perspective view. A stapling head sleeve retainer 360 is mounted on support shaft assembly 700 or on ferrule 720 or on tubular connector 640 in proximity to stapling head 600. Stapling head sleeve retainer 360 has generally hollow frustoconical form as shown in FIG. 13A or hollow cylindrical shaped form as shown in FIG. 13B. Stapling head sleeve retainer 360 was not shown in FIG. 1 where a generic surgical anastomosis stapling instrument was presented.

Stapling head sleeve retainer 360 forms a ring-shaped cavity 366 around support shaft assembly 700 or ferrule 720 or tubular connector 640. Cavity 366 is configured to be able to releasably engage and releasably hold a portion of stapling head sleeve 300 with one or more compressible/expandable rings 310, with compressible/expandable ring fitting into cavity 366 in a radially compressed configuration. The inner diameter of stapling head sleeve retainer 360 is smaller than the outside diameter of compressible/expandable ring 310 when compressible/expandable ring 310 is fully expanded.

Figure 14A:
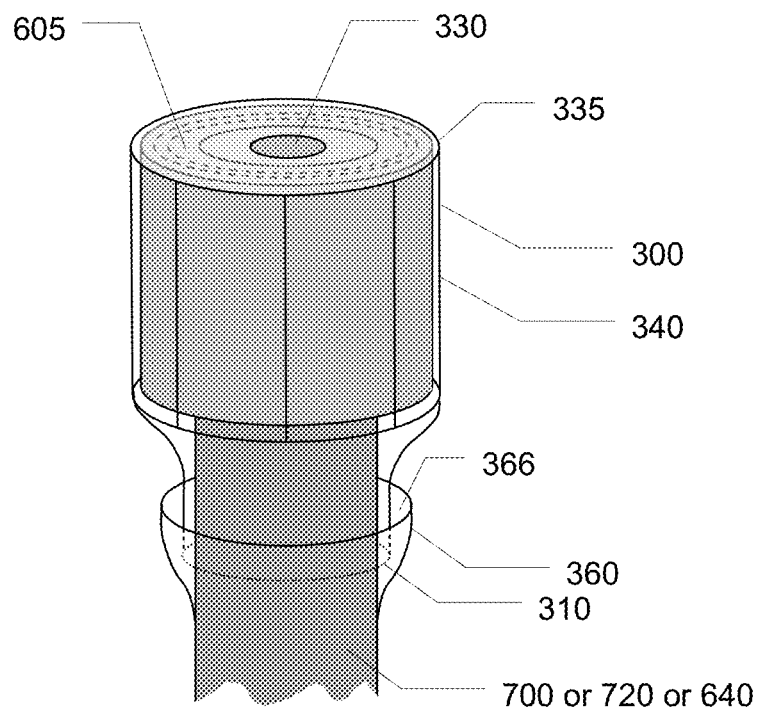
FIGS. 14A-B show schematic perspective views of stapling head and stapling head sleeve of the present invention.
Figure 14B:
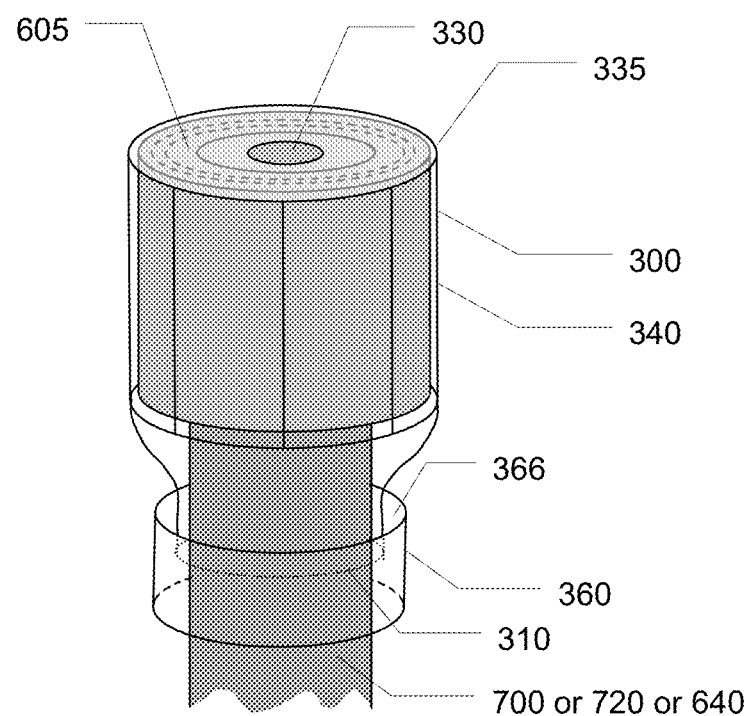

Referring now to FIGS. 14A and 14B, mounting of stapling head sleeve 300 on stapling head 600 with flange 335 positioned against tissue facing surface 605 and sleeve wall 340 is wrapped around stapling head 600. FIG. 14A shows how optional proximal compressible/expandable ring 310 is compressed and releasably packed into ring-shaped cavity 366 formed by frustoconical shaped stapling head sleeve retainer 360 of FIG. 13A.

FIG. 14B shows how optional proximal compressible/expandable ring 310 is compressed and releasably packed into ring-shaped cavity 366 formed by hollow cylindrical shaped stapling head sleeve retainer 360 of FIG. 13B.

Figure 15:
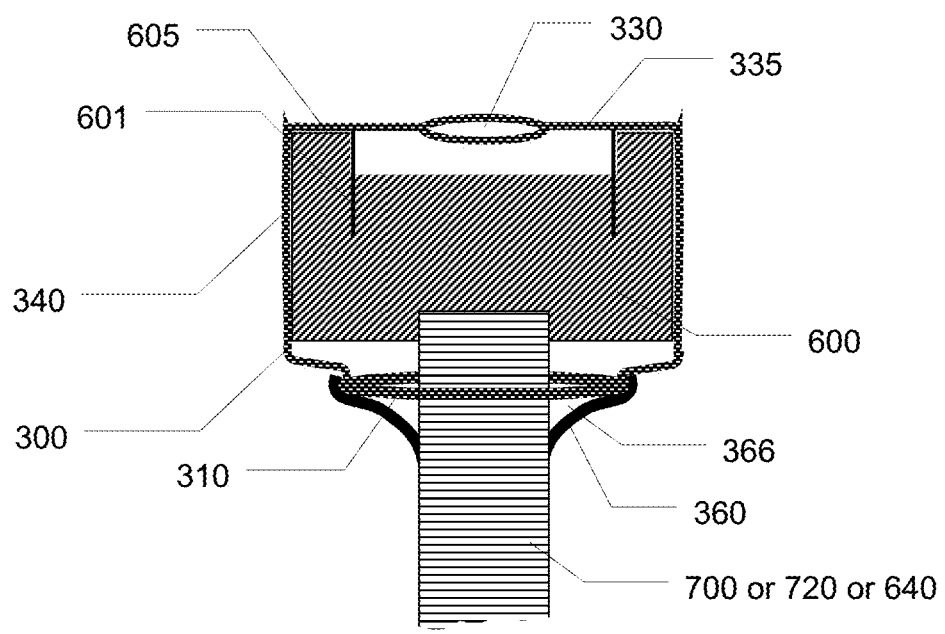
FIG. 15 shows schematic cross-sectional view of stapling head and stapling head sleeve of the present invention.

FIG. 15 shows the embodiment of FIG. 14A in a schematic cross-sectional view with stapling head sleeve 300 mounted onto stapling head 600 with flange 335 positioned against tissue facing surface 605 and sleeve wall 340 is wrapped around stapling head 600, with proximal compressible/expandable ring 310 compressed and releasably packed into ring-shaped cavity 366 formed by frustoconical shaped stapling head sleeve retainer 360 of FIGS. 13A and 14A.

As shown above, stapling head sleeve 300 which is made of polymeric, flexible, and at least partially elastic materials, is configured to releasably fit onto and around stapling head 600 with stapling head 600 substantially enveloped by stapling head sleeve 300 and positioned substantially inside hollow tubular stapling head sleeve 300.

Figure 16:
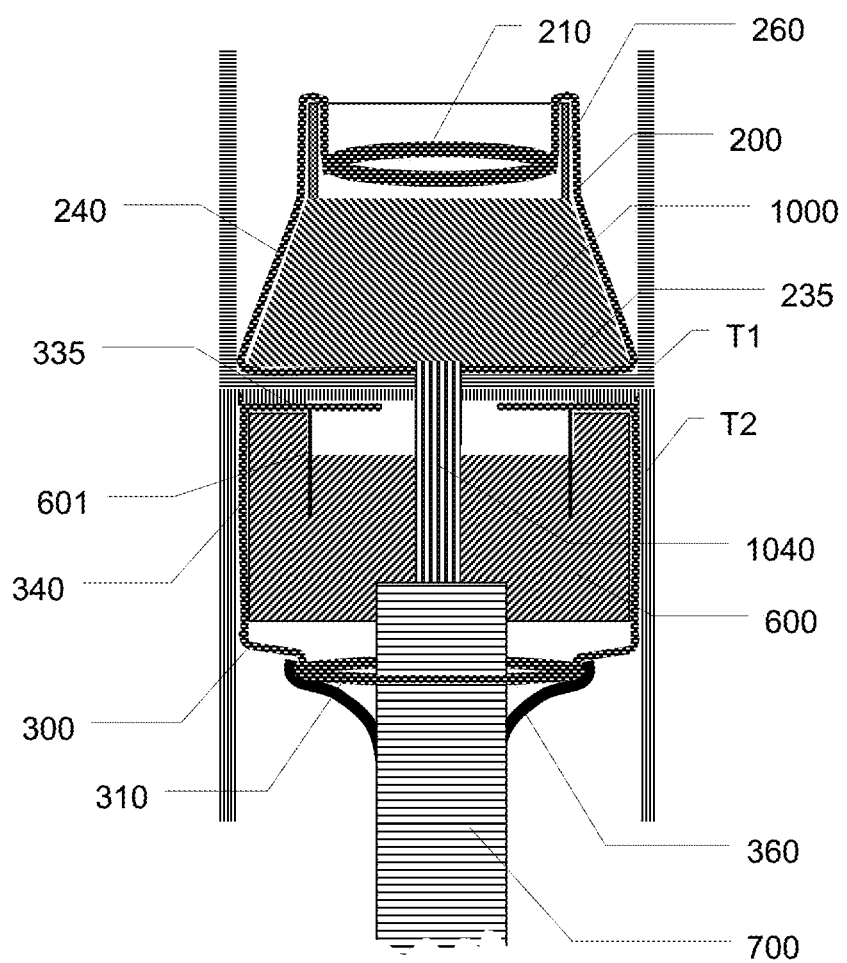
FIGS. 16 and 17 show schematic cross-sectional view of stapler of the present invention in operation.

Referring now to FIG. 16, a schematic cross-sectional partial view of a portion of circular stapler performing anastomotic joining of tubular tissues T1 and T2 is presented. Anvil 1000 is shown disposed within tubular tissue T1 and connected to stapling head 600 via moveable shaft 1040. Stapling head 600 is shown disposed within tubular tissue T2 and supported on support shaft assembly 700. For simplification, the mechanism of staples deployment and mechanism of deploying tissue cutting concentric knife 601 are not shown. FIG. 16 shows anvil 1000 and stapling head 600 approximated, compressing tissue T1 and T2 between them.

Anvil sleeve 200 is shown mounted on anvil 1000 with sleeve wall 240 wrapped around anvil 1000 and distal compressible/expandable ring 210 folded inward and radially compressed and releasably engaged inside sleeve retainer 260. Stapling head sleeve 300 is shown mounted onto stapling head 600 with sleeve wall 340 wrapped around stapling head 600, with proximal compressible/expandable ring 310 compressed and releasably packed into sleeve retainer 360.

Flange 235 of anvil sleeve 200 and flange 335 of stapling head sleeve 300 are disposed between stapling head 600 and anvil 1000, with flange 235 on tissue facing side of anvil sleeve 200 and flange 335 on tissue facing side of stapling head sleeve 300, with areas of tissues T1 and T2 which are to be stapled positioned between flange 235 and optional flange 335.

Figure 17:
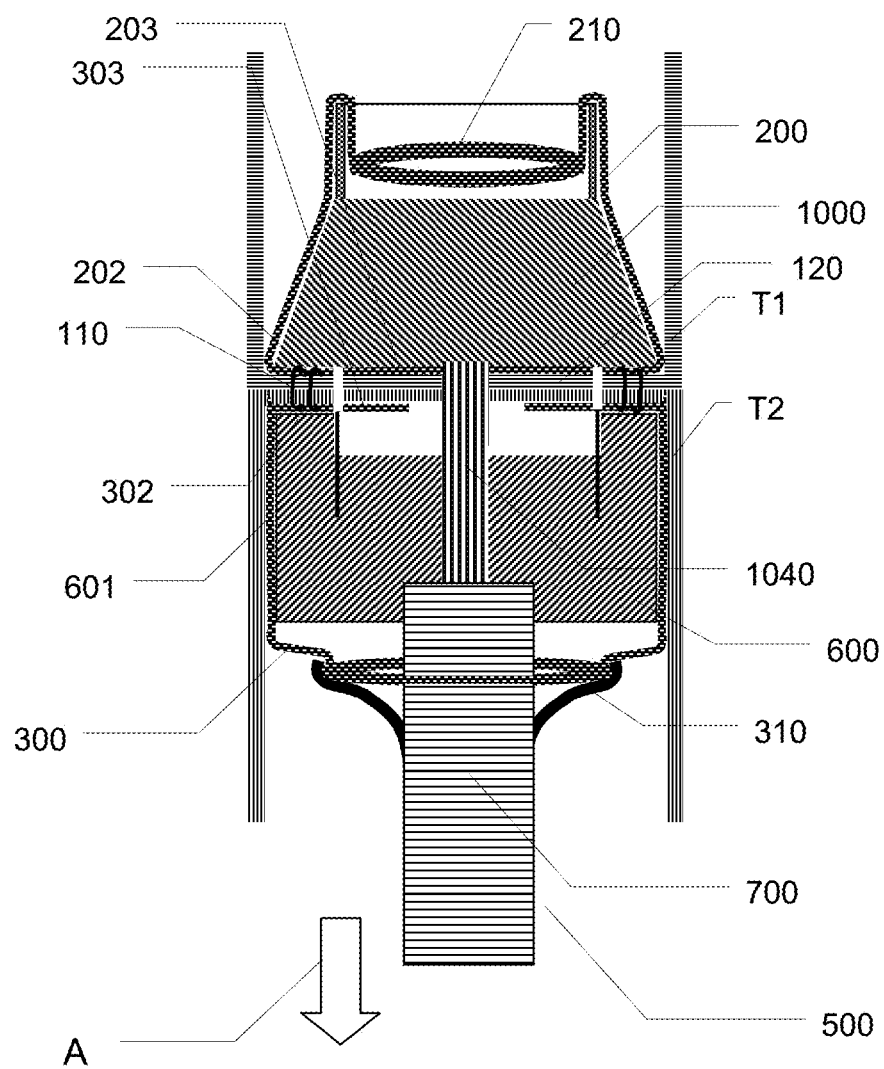

FIG. 17 shows the configuration when staples 110 fired thus establishing a stapled joint between tissues T1 and T2 with staples 110 concentrically arranged in one or more concentric rows around tissue donut or cut-out 120 which is formed by deploying and then retracting tissue cutting concentric knife 601. Areas 302 of stapling head sleeve 300 and areas 202 of anvil sleeve 200 which are opposing staples 110 rows are stapled to tissues T1 and T2. Areas 303 of stapling head sleeve 300 and areas 203 of anvil sleeve 200 which are opposing tissue cutting concentric knife 601 are cut by the action of knife 601 and are separated from respectively stapling head sleeve 300 and anvil sleeve 200.

After deploying staples 110 and cutting out tissue cutout 120 thus establishing the anastomotic joint, with stapling head sleeve 300 and anvil sleeve 200 stapled to tissue T1 and T2, circular stapler 500 is withdrawn in the direction of arrow A. As anvil 1000 moves past staples 110 in the direction of arrow A, with anvil sleeve proximal end immobilized on tissue by staples 110, anvil sleeve 200 is turned outside-in and inverted with compressible/expandable ring 210 released from sleeve retainer 260. As stapling head 600 moves in the direction of arrow A, with stapling head sleeve 300 distal end immobilized on tissue by staples 110, compressible/expandable ring 310 is released from sleeve retainer 360.

Figure 18:
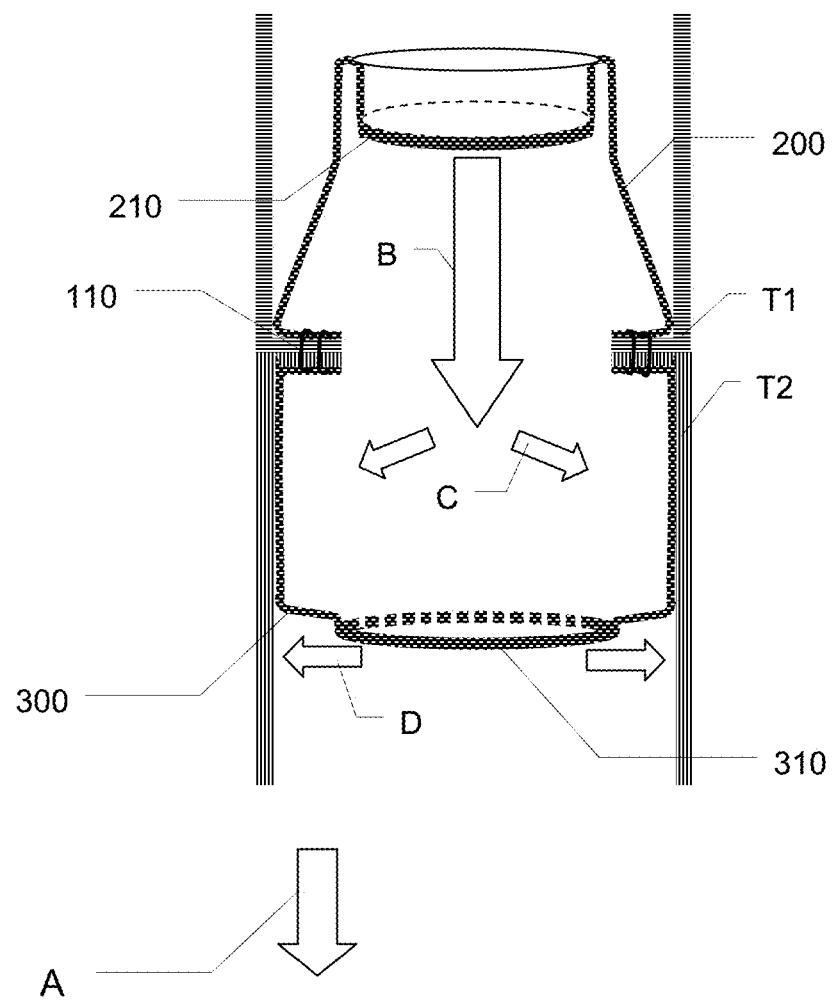
FIGS. 18 and 19 show schematic cross-sectional view of anvil sleeve and stapling head sleeve of the present invention in operation.

Referring now to FIG. 18, a schematic cross-sectional view of configuration shown in FIG. 17 is presented, omitting circular stapler 500. Arrow B shows the direction where anvil sleeve 200 distal end is pulled by anvil 1000 (not shown), with arrows C showing the direction of expansion of compressible/expandable ring 210 as ring 210 is released from sleeve retainer 260 (not shown) after anvil 1000 passed anastomotic joint formed by staples 110. Anvil sleeve 200 thus is turned outside-in and inverted with compressible/expandable ring 210 which was positioned prior to deployment inside tissue lumen T1, is released from sleeve retainer 260 and deployed inside tissue T2.

Arrows D are showing the direction of expansion of compressible/expandable ring 310 as ring 310 is released from sleeve retainer 360 (not shown) after stapling head 600 advances in the direction of arrow A. Thus compressible/expandable ring 310 of stapling head sleeve 300 was positioned prior to deployment inside tissue lumen T2, is released from sleeve retainer 360 and deployed also inside tissue T2.

Figure 19:
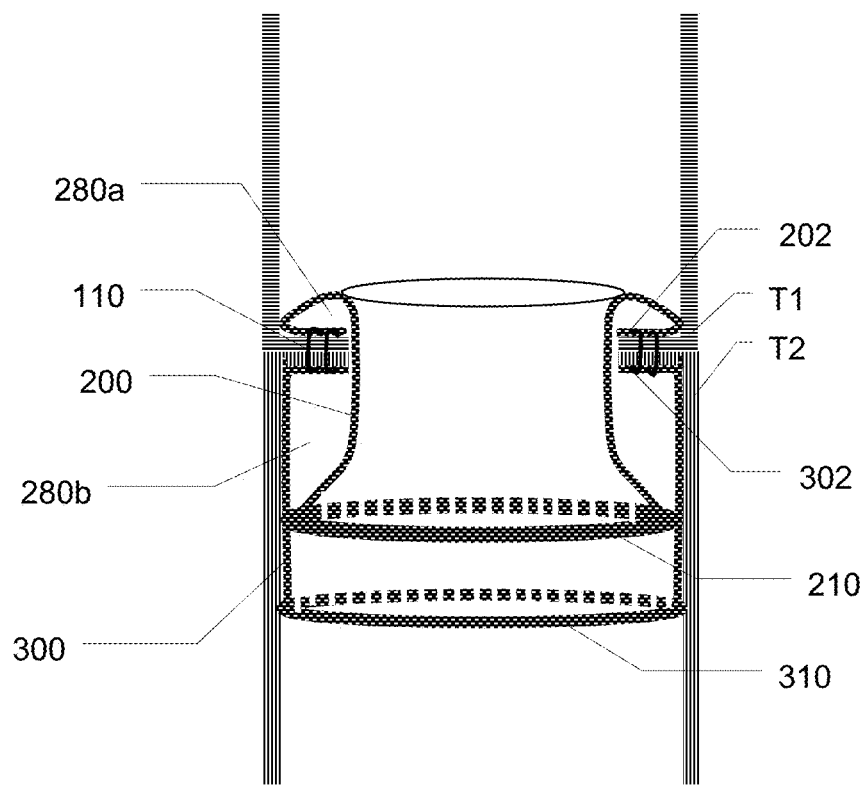

Referring now to FIG. 19, a schematic cross-sectional view of configuration after removal of circular stapler 500 and deployment of anvil sleeve 200 and stapling head sleeve 300 around and onto anastomotically joined tissue lumens T1 and T2. Anvil sleeve 200 is stapled to tissues T1 and T2 within tissue lumen T1 and then inverted/turned outside-in, passes over area of tissues T1 and T2 stapled by staples 110, extending from tissue lumen T1 into tissue lumen T2, and then completes forming pockets or enclosures 280a and 280b around inside of anastomotic joint by isolating anastomotic joint from the environment inside tissue lumens T1 and T2. Pocket 280a is shown formed above anastomotic joint inside tissue T1 and pocket 280b is shown formed below anastomotic joint inside tissue T2. Compressible/expandable ring 210 expands and pushes against tissue lumen T2 wall inside surface, creating an isolated sealed pockets or enclosures 280a and 280b around the areas of resected and stapled tissue.

As further shown in FIG. 19, optionally, stapling head sleeve 300 is deployed inside tissue lumen T2. Stapling head sleeve 300 is stapled to tissues T1 and T2 and is fully positioned within tissue lumen T2 and extends along tissue lumen T2. As shown, optional compressible/expandable ring 310 expands and pushes against tissue lumen T2 wall inside surface, with compressible/expandable ring 210 positioned against stapling head sleeve 300 inside tissue lumen T2 between optional compressible/expandable ring 310 and areas of tissue stapled by staples 110. In this embodiment, optional stapling head sleeve 300 provides additional protection to tissues T1 and T2 in forming isolating pockets or enclosures 280b around the areas of resected and stapled tissue.

Figure 20:
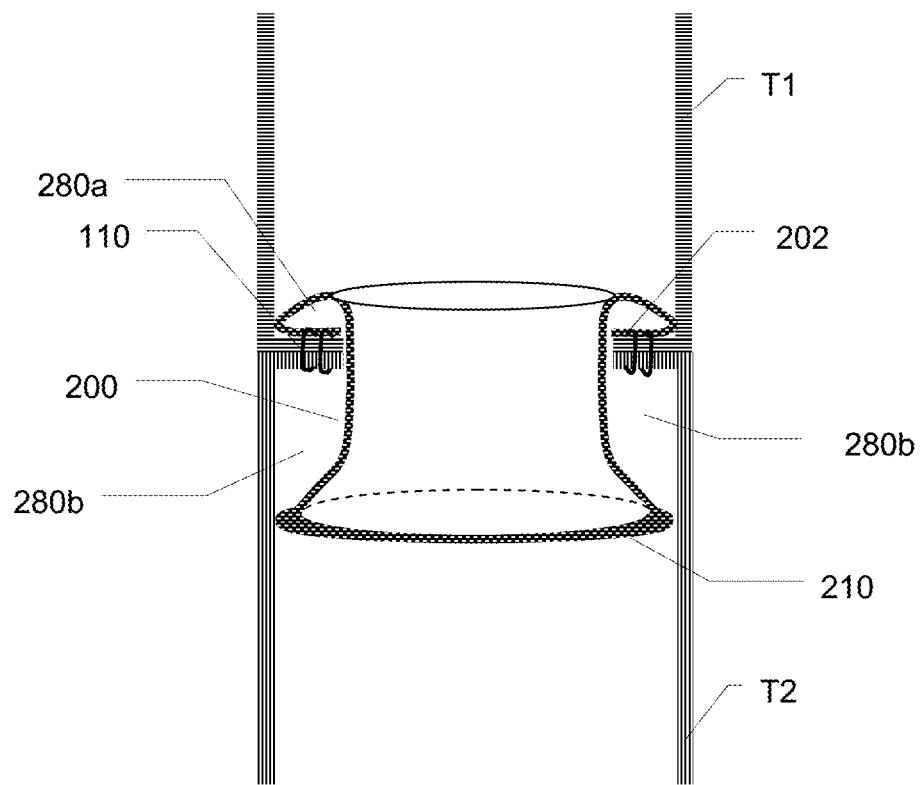
FIG. 20 shows schematic cross-sectional view of anvil sleeve of the present invention in operation.

Referring now to FIG. 20, a schematic cross-sectional view of configuration after removal of circular stapler 500 and deployment of anvil sleeve 200 is shown, whereby there is no optional stapling head sleeve 300. Anvil sleeve 200 is stapled to tissues T1 and T2 within tissue lumen T1 and then inverted/turned outside-in, passes over area of tissues T1 and T2 stapled by staples 110, extending from tissue lumen T1 into tissue lumen T2, and then completes forming a pockets or enclosures 280a and 280b around inside of anastomotic joint by isolating anastomotic joint from the environment inside tissue lumens T1 and T2. Compressible/expandable ring 210 expands and pushes directly against tissue lumen T2 wall inside surface, creating isolated sealed pockets or enclosures 280a and 280b around the areas of resected and stapled tissue.

Figure 21:
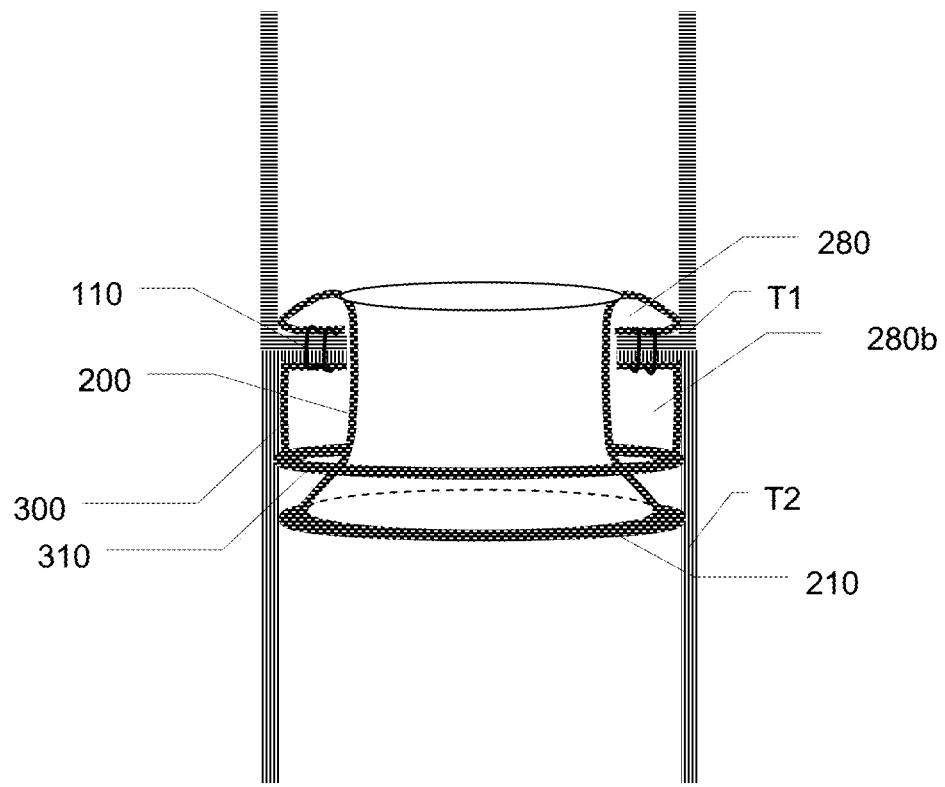
FIGS. 21 and 22 show schematic cross-sectional view of anvil sleeve and stapling head sleeve of the present invention in operation.

In the embodiment shown in FIG. 21, similarly to embodiment of FIG. 19, both anvil sleeve 200 and stapling head sleeve 300 are deployed around and onto anastomotically joined tissue lumens T1 and T2. In this embodiment, Anvil sleeve 200 extends beyond stapling head sleeve 300, with compressible/expandable ring 210 positioned directly against tissue T2 and optional compressible/expandable ring 310 positioned between compressible/expandable ring 210 and areas of tissue stapled by staples 110.

Figure 22:
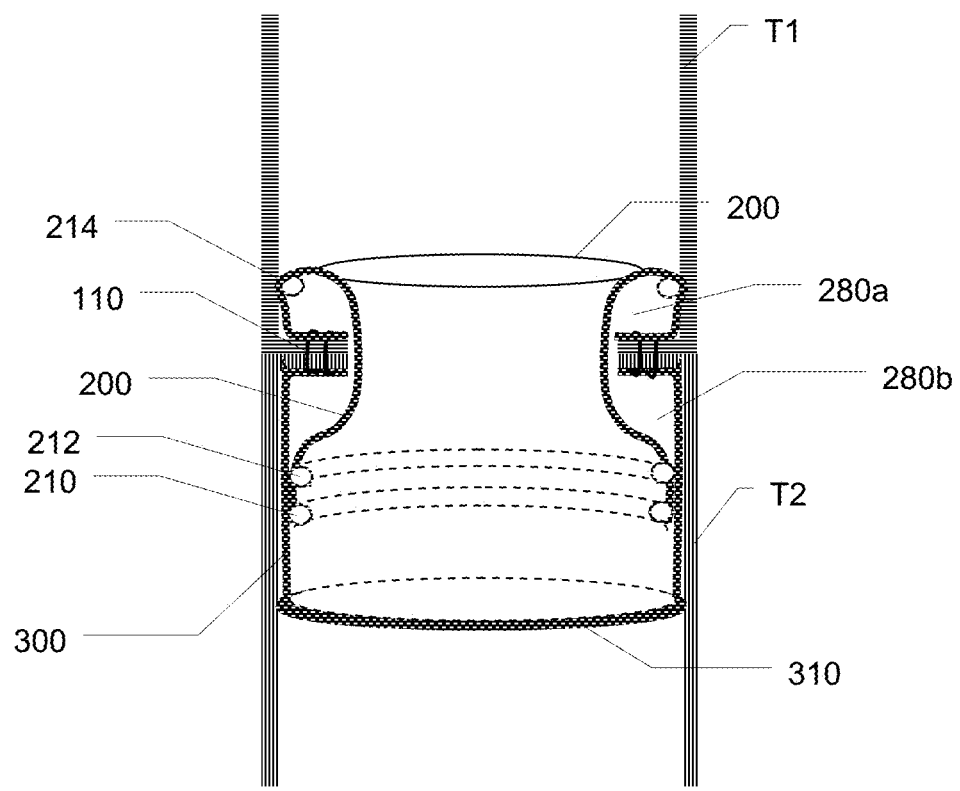

The embodiment shown in FIG. 22 is similar to the embodiment of FIG. 19 in that both anvil sleeve 200 and optional stapling head sleeve 300 are present. Anvil sleeve 200 has construction similar to embodiments of FIGS. 5B and 5D, whereby anvil sleeve 200 has compressible/expandable rings 210 and 212 which provide for an improved seal within tissue lumen T2. Anvil sleeve 200 also has compressible/expandable ring 214 which provides for additional sealing against tubular tissue lumen T1. Isolated sealed pockets or enclosures 280a and 280b around the areas of resected and stapled tissue is formed by anvil sleeve 200 and optional stapling head sleeve 300.

Advantageously, in some embodiments, isolated sealed pockets or enclosures 280a and 280b extend above and below the immediate vicinity of the established anastomotic joint. This is beneficial to protect vulnerable tissues around the anastomotic joint, which are also subject to ulceration and leaks.

According to one embodiment of the present invention, the sequence of using anvil sleeve 200 and optional stapling head sleeve 300 of the present invention while establishing an anastomotic joint and isolating and protecting said anastomotic joint is as follows:

a) Axially positioning anvil sleeve 200 on anvil 1000 and releasably packing/engaging compressible/expandable ring 210 in anvil sleeve retainer 260;
b) Axially inserting anvil 1000 into tubular tissue T1 and closing tissue T1 around anvil 1000;
c) Optionally axially positioning optional stapling head sleeve 300 on stapling head 600 and optionally releasably packing/engaging optional compressible/expandable ring 310 in stapling head sleeve retainer 360;
d) Axially inserting stapling head 600 into tubular tissue T2;
e) Connecting anvil 1000 to stapling head 600 via anvil shaft 1040;
f) Approximating anvil 1000 and stapling head 600 and compressing tubular tissues T1 and T2 between stapling head 600 and anvil 1000;
g) Firing anastomotic stapler 500 and establishing stapled anastomotic joint between tissues T1 and T2 and simultaneously stapling anvil sleeve 200 and optional stapling head sleeve 300 to tissues T1 and T2;
h) Withdrawing anastomotic stapler 500 from tissue lumens T1 and T2 thus releasing compressible/expandable ring 210 and optional compressible/expandable ring 310 and leaving anvil sleeve 200 and optional stapling head sleeve 300 inside tissue lumens T1 and T2, while anvil sleeve 200 is turned outside-in and inverted and deployed inside tissue T2, with optional stapling head sleeve 300 is simultaneously optionally deployed inside tissue T2;
i) Allowing compressible/expandable ring 210 and optional compressible/expandable ring 310 expand and push against tissue lumen T2 wall inside surface, creating isolated sealed pockets or enclosures 280a and 280b around the areas of resected and stapled tissue, whereby anvil sleeve 200 extends from its end stapled to tissue T1 over the resected/stapled areas of tissues T1 and T2 and into tissue lumen T2 where the opposite end of anvil sleeve 200 having compressible/expandable ring 210 is then positioned; and
j) Leaving anvil sleeve 200 and optional stapling head sleeve 300 inside tissue lumens T1 and T2 until at least partial healing of tissues at the established anastomotic joint.

Complete steps of anastomotic surgical procedures, e.g. application of purse string sutures are not listed above, but will be known to skilled artisans. Additional steps after the installation include:

k) Optionally releasing medicants accelerating healing and/or preventing infection from anvil sleeve 200 and/or optional stapling head sleeve 300;
l) Optionally releasing a specialized microflora anvil sleeve 200 and/or optional stapling head sleeve 300; and m) Allowing the sleeves to pass through the GI tract out of the body after a period of from 3 days to about 8 weeks, more preferably 1 week, 2 weeks, 3 weeks, 4 weeks, or 6 weeks.

In certain embodiments anvil sleeve 200 and optional stapling head sleeve 300 are made of non-resorbable polymers or composites, preferably from polymeric and elastomeric materials. In one embodiment, sleeves are made of materials with low elasticity, low elastomeric properties materials, while compressible/expandable rings 210, 310 are made of elastomeric compressible/expandable materials, which are made of at least partially resorbable or erodible/soluble materials. Sleeves 200 and 300 are excreted as the stapled areas of tissues T1 and T2 eventually undergo necrotic transformation and die off.

In certain embodiments anvil sleeve 200 and optional stapling head sleeve 300 are made of at least partially resorbable or erodible/soluble materials which are known to a skilled artisan, with time to at least partially dissolve from about 3 days to about 30 days in the gastro-intestinal (GI) tract, such as 1 week, 2 weeks, 3 weeks, or 4 weeks, most preferably 2-4 weeks. Particularly expandable/compressible rings 210, 310 are made of soluble/erodible or resorbable materials resulting in releasing of anvil sleeve 200 and optional stapling head sleeve 300 from engaging with tissue T1 and T2 walls. This release can happen before, after, or at about the same time as stapled areas of tissues T1 and T2, to which sleeves 200 and 300 are stapled, undergo necrotic transformation and die off.

In some embodiments, sleeves 200 and 300 walls 240, 340 are made from non-resorbable polymers or composites, while expandable/compressible rings 210, 310 made of soluble/erodible or resorbable materials resulting in releasing of anvil sleeve 200 and optional stapling head sleeve 300 from engaging with tissue T1 and T2 walls when expandable/compressible rings 210, 310 have significantly dissolved/eroded or resorbed.

In certain embodiments, compressible/expandable rings 210, 310 are tubular, hollow pre-inflated circular rings which are then packed and/or folded or compacted into sleeve retainers. Upon release form sleeve retainers, rings assume their expanded inflated shape with external diameter close to the internal diameter of tissue lumens or exceeding the internal diameter of tissue lumens by 5-30%, such as 10% or 20%.

Advantageously, isolated sealed pockets or enclosures 280a and 280b around the areas of resected and stapled tissue that is formed by anvil sleeve 200 and optional stapling head sleeve 300 creates an environment isolated from the main tissue lumens T1 and T2, such as GI tract.

According to the present invention, in addition to isolating the areas of resected and stapled tissue for GI environments, there is provided an optional release of medicants accelerating healing and/or preventing infection. The medicants can be released into pockets or enclosures 280a and 280b from anvil sleeve 200 and/or optional stapling head sleeve 300. Further, a specialized microflora can be released into pockets or enclosures 280a and 280b from anvil sleeve 200 and/or optional stapling head sleeve 300.

According to the present invention, anvil sleeve 200 and/or optional stapling head sleeve 300 are optionally at least partially coated or impregnated with releasable antimicrobial agents. All portions of sleeve 200 can be treated with such agents, or specific portions which are in contact with areas of tissues T1 and T2 or specific portions which are facing pockets or enclosures 280a and 280b, are preferably coated or impregnated with releasable antimicrobial agents.

Advantageously, pockets or enclosures 280a and 280b isolate areas of stapled and cut tissue from the GI environment and enables establishment of higher sustained concentration of anti-microbial agents or other medicants, such as specific microflora, in the immediate vicinity of these areas of tissue. Such treatment is thought to minimize formation of tissue ulcerations and other defects and decrease the occurrence of anastomotic leaks.

External diameter of compressible/expandable rings 210, 212, 214, 310, 312 in expanded form is approximately equal or larger that the internal diameter of the tissue lumen that is being anastomotically joined, such as 0%-50% larger, such as 5%, 10%, 20%, 30%, 50% larger, most preferably 10%, 15%, 20% larger than ID of tissue lumen such as T1 or T2. The compressible/expandable rings are configured, when expanded, to snugly fit inside tissue lumens T1 and T2 and create a tight seal against internal surface of the tissue lumen but without significantly expanding and stressing tissue lumen outwards.

Thickness of sleeves 200 and 300 walls 240, 340, is from about 20 microns to about 2 mm, more preferably from 50 microns to 1 mm, such as 50, 100, 200, 300, 500 microns.

The diameter of openings 230, 330 is generally configured to fit shaft 1040 and is from about 3 mm to about 10 mm.

The length of anvil sleeve 200 is configured to enable sleeve 200 to be turned outside-in and extend from stapled areas of tissue T1 to below stapled area of tissue T2 but still remain fully within GI tract. In some embodiments, the length of sleeve 200 is from about 10 mm to about 75 mm, more preferably 15 mm to 50 mm, such as 15, 20, 25, 30, 40, 50 mm. The length of stapling head sleeve 300 is from about 5 mm to about 75 mm, more preferably 10 mm to 40 mm, such as 10, 15, 20, 30, 40 mm.

In some embodiments there are micro-apertures (not shown) formed in anvil sleeve 200, which help to relieve any pressure build-up in pockets or enclosures 280a and 280b. In some embodiments, there are one way valve flaps (not shown) formed in anvil sleeve 200, which help to relieve any pressure build-up in pockets or enclosures 280a and 280b.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

What is claimed is:

1. A circular stapling instrument comprising:
   a) an anvil having a tissue facing end and an opposite distal end, with an anvil sleeve retainer positioned on the distal end thereof;
   b) a cylindrical stapling head mounted on a support shaft, said stapling head containing a plurality of deployable staples in concentric arrays on a tissue facing side and a concentric knife;
   c) a moveable shaft connecting the anvil and stapling head;
   d) an elongated tubular hollow anvil sleeve,
   wherein said anvil sleeve has a compressible and expandable anvil ring at a distal end thereof,
   said anvil sleeve is releasably mounted on said anvil and at least partially enveloping said anvil,
   said anvil ring is compressed and releasably engaged by the anvil sleeve retainer and a portion of said anvil sleeve is disposed on the tissue facing end of said anvil, wherein said anvil sleeve retainer is a hollow cup having diameter smaller than diameter of said cylindrical stapling head, said anvil ring is configured to expand when released from said anvil sleeve retainer, wherein said anvil sleeve at the distal end thereof is inverted or turned outside-in and releasably packed into said anvil sleeve retainer.

2. The circular stapling instrument of claim 1, wherein said anvil sleeve retainer is a ring-shaped cavity having diameter smaller than diameter of said cylindrical stapling head.

3. The circular stapling instrument of claim 1, wherein said anvil sleeve has an opening at a proximal end thereof, said opening configured to allow feeding of said moveable shaft through said opening.

4. The circular stapling instrument of claim 1, wherein said anvil sleeve further comprises a buttress disposed at the tissue facing end of said anvil.

5. The circular stapling instrument of claim 1, wherein at least a portion of said anvil sleeve is erodible, dissolvable, or resorbable in a mammalian gastrointestinal tract over a period ranging from 1 to 8 weeks.

6. The circular stapling instrument of claim 1, wherein said anvil ring is erodible, dissolvable, or resorbable in a mammalian gastrointestinal tract over a period ranging from 1 to 8 weeks.

7. The circular stapling instrument of claim 1, wherein said anvil sleeve is at least partially coated or impregnated with a releasable anti-bacterial, anti-microbial, anti-infective agent, bacterial culture, or combinations thereof.

8. The circular stapling instrument of claim 1, further comprising
   a) an elongated tubular hollow stapling head sleeve,
   wherein said stapling head sleeve releasably mounted on said stapling head and at least partially enveloping said stapling head and a portion of said stapling head sleeve is disposed on the tissue facing side of said stapling head.

9. The circular stapling instrument of claim 8, wherein the stapling head sleeve further comprises a compressible and expandable stapling head sleeve ring at a proximal end thereof.

10. The circular stapling instrument of claim 9, further comprising a stapling head sleeve retainer positioned on the support shaft configured to releasably engage said stapling head sleeve.

11. The circular stapling instrument of claim 10, wherein said stapling head sleeve retainer has a hollow frustoconical or a hollow cylindrical form and forms a ring-shaped cavity around said support shaft, wherein the diameter of said ring-shaped cavity is smaller than diameter of said cylindrical stapling head.

12. The circular stapling instrument of claim 11, wherein said compressible and expandable stapling head sleeve ring is radially compressed to a diameter smaller than diameter of said cylindrical stapling head.

13. The circular stapling instrument of claim 8, wherein said stapling head sleeve has an opening at a distal end thereof, said opening configured to allow feeding of said moveable shaft through said opening.

14. The circular stapling instrument of claim 8, wherein said stapling head sleeve further comprises a buttress disposed at the tissue facing side of said stapling head.

15. The circular stapling instrument of claim 8, wherein at least a portion of said stapling head sleeve is erodible, dissolvable, or resorbable in a mammalian gastrointestinal tract over a period ranging from 1 to 8 weeks.

16. The circular stapling instrument of claim 8, wherein said stapling head sleeve is erodible, dissolvable, or resorbable in a mammalian gastrointestinal tract over a period ranging from 1 to 8 weeks.

17. The circular stapling instrument of claim 8, wherein said anvil sleeve is at least partially coated or impregnated with a releasable anti-bacterial, anti-microbial, anti-infective agent, bacterial culture, or combinations thereof.

18. A method of establishing an anastomotic joint between tubular tissue lumens with an anastomotic stapler, the stapler having a stapling head containing a plurality of deployable staples, the method comprising the steps of:
   a) axially positioning a hollow tubular anvil sleeve having a compressible/expandable anvil ring on one end thereof on the anvil and releasably engaging said compressible/expandable anvil ring in an anvil sleeve retainer mounted on said anvil;
   b) axially inserting said anvil into a first tubular tissue and closing said first tubular tissue around said anvil;
   c) axially inserting said stapling head into a second tubular tissue;
   d) connecting said anvil to said stapling head via an anvil shaft;
   e) approximating said anvil and said stapling head to compress said first and second tubular tissues between said stapling head and said anvil;
   f) firing said anastomotic stapler to form a stapled anastomotic joint between said first and second tubular tissues and simultaneously stapling said anvil sleeve to said first and second tubular tissues;
   g) withdrawing said anastomotic stapler from said first and second tubular tissues to release said compressible/expandable anvil ring form said anvil sleeve retainer and leave said anvil sleeve inside said first and second tubular tissues,
   h) turning and inverting said anvil sleeve outside-in;
   i) extending said anvil sleeve from said first tubular tissue into said second tubular tissue;
   j) expanding said compressible/expandable anvil ring to push against said second tissue lumen inside surface; and
   k) leaving said anvil sleeve inside said first and second tubular tissues for sufficient time for at least partial healing of said tissues at the anastomotic joint.

* * * * *